United States Patent
Richens et al.

(10) Patent No.: US 11,017,905 B2
(45) Date of Patent: May 25, 2021

(54) COUNTERFACTUAL MEASURE FOR MEDICAL DIAGNOSIS

(71) Applicant: Babylon Partners Limited, London (GB)

(72) Inventors: Jonathan George Richens, London (GB); Ciarán Mark Lee, London (GB); Saurabh Johri, London (GB)

(73) Assignee: Babylon Partners Limited, London (GB)

( * ) Notice: Subject to any disclaimer, the term of this patent is extended or adjusted under 35 U.S.C. 154(b) by 0 days.

(21) Appl. No.: 16/520,280

(22) Filed: Jul. 23, 2019

(65) Prior Publication Data

US 2020/0279655 A1     Sep. 3, 2020

Related U.S. Application Data

(60) Provisional application No. 62/812,226, filed on Feb. 28, 2019.

(51) Int. Cl.
*G16H 50/50* (2018.01)
*G06N 5/04* (2006.01)
(Continued)

(52) U.S. Cl.
CPC ............ *G16H 50/50* (2018.01); *G06N 5/04* (2013.01); *G06N 7/005* (2013.01); *G16H 50/30* (2018.01); *G16H 70/60* (2018.01)

(58) Field of Classification Search
CPC ........ G16H 50/20; G16H 50/50; G16H 50/70; G16H 50/30; G16H 70/60; G06N 7/005; G06N 5/04
See application file for complete search history.

(56) References Cited

U.S. PATENT DOCUMENTS

2007/0288418 A1   12/2007   Pope
2008/0215367 A1*   9/2008   Marshall ............... G06Q 10/00
                                                                      705/3
(Continued)

FOREIGN PATENT DOCUMENTS

WO    2016-094330 A2   6/2016
WO    2016-097886 A1   6/2016

OTHER PUBLICATIONS

Shpitser, Ilya, "Complete Identification Methods for the Causal Hierarchy," Journal of Machine Learning Research 9 (2008), 1941-1979 (Year: 2008).*

(Continued)

*Primary Examiner* — John P Go
(74) *Attorney, Agent, or Firm* — McDermott Will & Emery LLP

(57) ABSTRACT

A method for providing a computer-implemented medical diagnosis includes receiving an input from a user comprising at least one symptom of the user. The method also includes providing the at least one symptom as an input to a medical model, the medical model being retrieved from memory. The medical model includes a probabilistic graphical model comprising probability distributions and relationships between symptoms and diseases. The method also includes performing inference on the probabilistic graphical model to obtain a prediction of the probability that the user has that disease. The method also includes outputting an indication that the user has a disease from the Bayesian inference, wherein the inference is performed using a counterfactual measure.

12 Claims, 9 Drawing Sheets

(51) Int. Cl.
  *G16H 70/60* (2018.01)
  *G16H 50/30* (2018.01)
  *G06N 7/00* (2006.01)

(56) References Cited

U.S. PATENT DOCUMENTS

| | | | |
|---|---|---|---|
| 2011/0137847 | A1 | 6/2011 | Fahner |
| 2014/0046696 | A1* | 2/2014 | Higgins .............. G06F 19/3456 705/3 |
| 2017/0061324 | A1* | 3/2017 | Glass ..................... G06N 7/005 |
| 2019/0155993 | A1* | 5/2019 | Wilkerson ............. G16H 50/20 |
| 2019/0332957 | A1* | 10/2019 | Malur Srinivasan .. G06N 7/005 |

OTHER PUBLICATIONS

Liu, Y., et al., "Passive diagnosis for wireless sensor networks," IEEE/ACM Trans-actions on Networking (TON), vol. 18, No. 4, pp. 1132-1144, 2010.
Perreault, L., et al., "A noisy-or model for continuous time bayesian networks.," in FLAIRS Conference, pp. 668-673, 2016.
Arora, S., et al., "Provable learning of noisy-or networks," in Proceedings of the 49th Annual ACM SIGACT Symposium on Theory of Computing, pp. 1057-1066, ACM, 2017.
Abdollahi, A., et al., "Unification of leaky noisy or and logistic regression models and maximum a posteriori inference for multiple fault diagnosis using the unified model," in DX Conference (Denver, CO), 2016.
Pearl, J., "Probabilities of causation: three counterfactual interpretations and their identification," Synthese, vol. 121, No. 1-2, pp. 93-149, 1999.
Rota, G.C., "On the foundations of combinatorial theory i. theory of möbius functions," Probability theory and related fields, vol. 2, No. 4, pp. 340-368, 1964.
Johansson, F., et al., "Learning representations for counterfactual inference," in International Conference on Machine Learning, pp. 3020-3029, 2016.
Louizos, C., et al., "Causal effect inference with deep latent-variable models," in Advances in Neural Information Processing Systems, pp. 6446-6456, 2017.
Subbaswamy, A., et al., "Counterfactual normalization: Proactively addressing dataset shift using causal mechanisms," Proceedings of the 34th Conference on Uncertainty in Artificial Intelligence, arXiv:1808. 03253, 2018.
Schulam, P., et al., "Reliable decision support using counterfactual models," in Advances in Neural Information Processing Systems, pp. 1697-1708, 2017.
Buesing, L., et al., "Woulda, coulda, shoulda: Counterfactually-guided policy search," arXiv:1811.06272, 2018.
Liang, H., et al., "Evaluation and accurate diagnoses of pediatric diseases using artificial intelligence," Nature medicine, p. 1, 2019.
Topol, E.J., "High-performance medicine: the convergence of human and artificial intelligence," Nature medicine, vol. 25, No. 1, p. 44, 2019.
De Fauw, J., et al., "Clinically applicable deep learning for diagnosis and referral in retinal disease," Nature medicine, vol. 24, No. 9, p. 1342, 2018.
Silver, D., et al., "Mastering the game of go without human knowledge," Nature, vol. 550, No. 7676, p. 354, 2017.
Pearl, J., Causality. Chapter 7, Cambridge university press, 2009.
Trimble, M., et al., "The thinking doctor: clinical decision making in contemporary medicine," Clinical Medicine, vol. 16, No. 4, pp. 343-346, 2016.
Miller, R., "A history of the internist-1 and quick medical reference (qmr) computer-assisted diagnosis projects, with lessons learned," Yearbook of medical informatics, vol. 19, No. 01, pp. 121-136, 2010.
Cai, B., et al., "Bayesian networks in fault diagnosis," IEEE Transactions on Industrial Informatics, vol. 13, No. 5, pp. 2227-2240, 2017.
Yongli, Z., et al., "Bayesian networks-based approach for power systems fault diagnosis," IEEE Transactions on Power Delivery, vol. 21, No. 2, pp. 634-639, 2006.
Dey, S.., et al., "A bayesian network approach to root cause diagnosis of process variations," International Journal of Machine Tools and Manufacture, vol. 45, No. 1, pp. 75-91, 2005.
Cai, B., et al., "Multi-source information fusion based fault diagnosis of ground-source heat pump using bayesian network," Applied energy, vol. 114, pp. 1-9, 2014.
Lauritzen, S. L., Graphical models, vol. 17. pp. 28-32, Clarendon Press, 1996.
Miller, R. A., et al., "The internist-1/quick medical reference project—status report," Western Journal of Medicine, vol. 145, No. 6, p. 816, 1986.
Shwe, M. A., et al., "Probabilistic diagnosis using a reformulation of the internist-1/qmr knowledge base," Methods of Information in Medicine, vol. 30, No. 04, pp. 241-255, 1991.
Heckerman, D. E., et al., "Toward normative expert systems: Part i the pathfinder project," Methods of information in medicine, vol. 31, No. 02, pp. 90-105, 1992.
Morris, Q., "Recognition networks for approximate inference in bn20 networks," in Proceedings of the Seventeenth conference on Uncertainty in artificial intelligence, pp. 370-377, Morgan Kaufmann Publishers Inc., 2001.
Babylon Health, "Babylon health raises further 60m to continue building out ai doctor app," https://techcrunch.com/2017/04/25/babylon-health-raises-further-60m-to-continue-building-out-ai-doctor-app/, 2017.
Semigran, H. L., et al., "Evaluation of symptom checkers for self diagnosis and triage: audit study," bmj, vol. 351, p. h3480, 2015.
Amato, F., et al., "Artificial neural networks in medical diagnosis," 2013.
Das, R., et al., "Effective diagnosis of heart disease through neural networks ensembles," Expert systems with applications, vol. 36, No. 4, pp. 7675-7680, 2009.
Jiang, F., et al., "Artificial intelligence in healthcare: past, present and future," Stroke and vascular neurology, vol. 2, No. 4, pp. 230-243, 2017.
Neyman, J., "On the application of probability theory to agricultural experiments," 1990.
Rubin, D.B., "Bayesian inference for causal effects: The role of randomization," The Annals of statistics, pp. 34-58, 1978.
Richardson, T.S., et al., "Single world intervention graphs (swigs): A unification of the counterfactual and graphical approaches to causality," 2013.
Balke, A., et al., "Counterfactual probabilities: Computational methods, bounds and appli¬cations," in Proceedings of the Tenth international conference on Uncertainty in artificial intelli¬gence, pp. 46-54, Morgan Kaufmann Publishers Inc., 1994.
Shpitser, I., et al., and J. Pearl, "What counterfactuals can be tested," in Proceedings of the Twenty-Third Conference on Uncertainty in Artificial Intelligence, pp. 352-359, AUAI Press, 2007.
Bareinboim, E., et al., "Bandits with unobserved confounders: A causal approach," in Advances in Neural Information Processing Systems, pp. 1342-1350, 2015.
Razzaki, S., et al., "A comparative study of artificial intelligence and human doctors for the purpose of triage and diagnosis," arXiv preprint arXiv:1806.10698, 2018.
Nikovski, D., "Constructing bayesian networks for medical diagnosis from incomplete and partially correct statistics," IEEE Transactions on Knowledge & Data Engineering, No. 4, pp. 509-516, 2000.
Rish, I., et al., "Accuracy vs. efficiency trade-offs in probabilistic diagnosis," in AAAI/IAAI, pp. 560-566, 2002.
Onis'ko, A., et al., "Learning bayesian network parameters from small data sets: Application of noisy-or gates," International Journal of Approximate Reasoning, vol. 27, No. 2, pp. 165-182, 2001.
Halpern, Y., et al., "Unsupervised learning of noisy-or bayesian networks," arXiv preprint arXiv:1309.6834, 2013.
Guyatt, G. H., et al., "Measuring disease-specific quality of life in clinical trials.," CMAJ: Canadian Medical Association Journal, vol. 134, No. 8, p. 889, 1986.

(56) References Cited

OTHER PUBLICATIONS

Pearl, J., "Comment: understanding simpson's paradox," The American Statistician, vol. 68, No. 1, pp. 8-13, 2014.

Wellman, M. P., et al., "Explaining 'explaining away'," IEEE Transactions on Pattern Analysis and Machine Intelligence, vol. 15, No. 3, pp. 287-292, 1993.

Greenland, S., et al., "Causal diagrams for epidemiologic research," Epidemiology, vol. 10, pp. 37-48, 1999.

Shpitser, I., et al., "Effects of treatment on the treated: Identification and generalization," in Proceedings of the twenty-fifth conference on uncertainty in artificial intelligence, pp. 514-521, AUAI Press, 2009.

Morgan, S. L., et al., Counterfactuals and causal inference. Second Edition, Section 24, Cambridge University Press, 2015.

Pearl, J., et al., "Causal inference in statistics: An overview," Statistics surveys, vol. 3, pp. 96-146, 2009.

Pearl, J., "The mediation formula: A guide to the assessment of causal pathways in nonlinear models," tech. rep., California Univ Los Angeles Dept of Computer Science, 2011.

Pearl, J., "Direct and indirect effects," in Proceedings of the seventeenth conference on uncertainty in artificial intelligence, pp. 411-420, Morgan Kaufmann Publishers Inc., 2001.

Halpern, J. Y., Actual causality. Section 2.6 MiT Press, 2016.

Shpitser, I., et al., "What counterfactuals can be tested," arXiv preprint arXiv:1206.5294, 2012.

Romessis, C., et al., "Bayesian network approach for gas path fault diagnosis," Journal of engineering for gas turbines and power, vol. 128, No. 1, pp. 64-72, 2006.

Heckerman, D., "A tractable inference algorithm for diagnosing multiple diseases," in Machine Intelligence and Pattern Recognition, vol. 10, pp. 163-171, Elsevier, 1990.

EPO—Notification and of the International Search Report and the Written Opinion for related International Application No. PCT/GB2020/050490 dated May 25, 2020, 12 pgs.

\* cited by examiner

| Agent | Precision |
|---|---|
| Doctor 1 | 0.48 |
| Doctor 2 | 0.59 |
| Doctor 3 | 0.44 |
| Doctor 4 | 0.47 |
| Doctors (Mean) | 0.49 ± 0.05 |
| CDM (posterior) | 0.41 |
| CDM (counterfactual) | 0.48 |

COUNTERFACTUAL MEASURE FOR MEDICAL DIAGNOSIS

CROSS-REFERENCE TO RELATED APPLICATION

The present application claims the benefit of priority under 35 U.S.C. § 119 from U.S. Provisional Patent Application No. 62/812,226, entitled "COUNTERFACTUAL MEASURE FOR MEDICAL DIAGNOSIS," filed on Feb. 28, 2019, the disclosure of which is hereby incorporated by reference in its entirety for all purposes.

FIELD

Embodiments described herein relate to methods and systems for diagnosis using counterfactual measures.

BACKGROUND

Historically there has been much work towards designing algorithms that can perform medical diagnosis, with models containing hundreds of diseases and symptoms. Recently, there has been renewed hope that these algorithms could eventually surpass the accuracy of human doctors. To achieve this, it is necessary to consider how human doctors perform diagnosis. Given the symptoms presented by the patient and/or relevant knowledge of their background (such as age), a doctor attempts to determine the disease or diseases that are the most likely underlying cause of the symptoms presented. This approach is in contrast to the standard method used for algorithmic diagnosis, which involves ranking diseases by their posterior probabilities given the evidence presented, which is referred to as posterior ranking.

DETAILED DESCRIPTION

Figure 1:
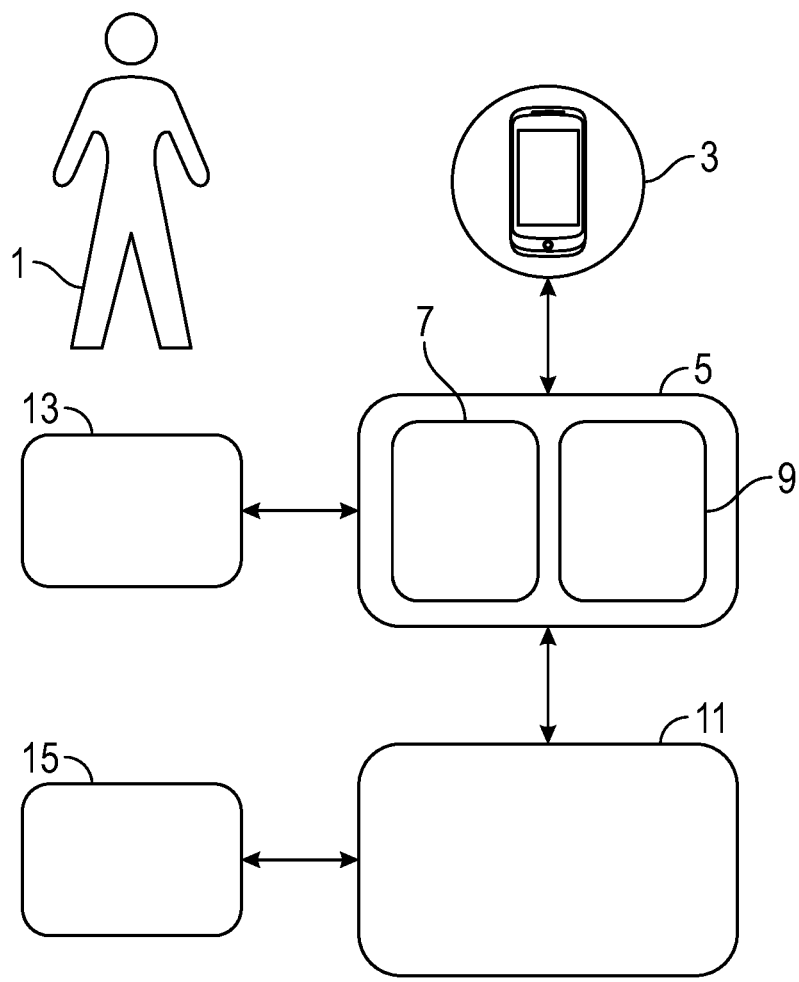
FIG. 1 is a schematic of a system in accordance with an embodiment.

In an embodiment, a method for providing a computer implemented medical diagnosis includes receiving an input from a user comprising at least one symptom of the user. The method also includes providing the at least one symptom as an input to a medical model, the medical model being retrieved from memory. The medical model includes a probabilistic graphical model comprising probability distributions and relationships between symptoms and diseases. The method also includes performing inference on the probabilistic graphical model to obtain a prediction of the probability that the user has that disease. The method also includes outputting an indication that the user has a disease from the Bayesian inference, wherein the inference is performed using a counterfactual measure.

The disclosed system provides an improvement to computer functionality by allowing computer performance of a function not previously performed by a computer. Specifically, the disclosed system provides for a diagnosis system that can provide counterfactual diagnosis that can provide better accuracy in diagnosis. Also, some of the embodiments allows a computationally more efficient diagnosis.

Although, medical diagnosis is exemplified in the description, the method can be applied to any diagnostic problem.

In one embodiment, the counterfactual measure is the expected disablement. In a further embodiment, the probabilistic graphical model is a Noisy-OR model.

In a further embodiment, the counterfactual measure is the expected disablement and the probabilistic graphical model is a Noisy-OR model. This combination allows a closed form solution that only requires knowledge of the observational statistics, as is the case for posterior ranking.

In a yet further embodiment, approximate inference techniques are used, for example, importance sampling. In a yet further embodiment, performing inference comprises using a discriminative model pre-trained to approximate the probabilistic graphical model, the discriminative model being trained using samples from said probabilistic graphical model. Performing inference may also include deriving estimates, from the discriminative model, that the user has a disease. Performing inference may also include performing approximate inference on the probabilistic graphical model to obtain an indication that the user has that disease using the estimate from the discriminative model.

In a further embodiment, the results of predictions of the diseases from the probabilistic graphical model are ranked using the counterfactual measure.

In a further embodiment, the probabilistic graphical model may be a so-called a twin network. The use of a twin network reduces computing counterfactual statements to performing Bayesian inference on an associated causal model.

In a further embodiment, the probabilistic graphical model is a twin network, and the counterfactual measure is the expected disablement. In a further embodiment, the probabilistic graphical model is a twin network, the counterfactual measure is the expected disablement and the probabilistic graphical model is a Noisy-OR model.

In a further embodiment, a system for providing a computer implemented medical diagnosis is provided, the system comprising a processor and a memory, the processor being adapted to receive an input from a user comprising at least one symptom of the user. The processor is also adapted to provide the at least one symptom as an input to a medical model, the medical model being retrieved from memory, the medical model comprising a probabilistic graphical model being stored in memory comprising probability distributions and relationships between symptoms and diseases. The processor is also adapted to perform inference on the probabilistic graphical model to obtain a prediction of the probability that the user has that disease. The processor is also adapted to output an indication that the user has a disease from the Bayesian inference, wherein the inference is performed using a counterfactual measure.

In a further embodiment, a method of forming a twin model that is a graphical representation for computing a counterfactual measure for medical diagnosis is provided. The method comprises receiving a set of data; creating a first graphical representation from the set of data, the first graphical representation comprising a plurality of first nodes indicating symptoms, risk factors and diseases, the first graphical representation indicating a relationship between the symptoms, the risk factors and the diseases; creating a second graphical representation, wherein the second graphical representation is a copy of the first graphical representation, the second graphical representation comprising a plurality of second nodes indicating the symptoms, the risk factors and the diseases; combining the first graphical representation and the second graphical representation to create said twin model; and setting an intervention node of the plurality of second nodes in the twin model to a value so that inference can be performed on the twin model to obtain a prediction of the probability that a user of the model has a specified disease.

This approach massively amortizes the standard inference cost of calculating counterfactuals by abduction, action and prediction, which would otherwise be intractable for large clinical diagnostic models (CDMs).

In a yet further embodiment, each node in the plurality of first nodes is associated with a latent variable, and the method further comprises: linking the first graphical representation and the second graphical representation by sharing the latent variables of each node of the plurality of first nodes with a corresponding node in the plurality of second nodes.

In a yet further embodiment, the first graphical representation and the second graphical representation are probabilistic graphical models.

In a yet further embodiment, the first graphical representation and the second graphical representation are Noisy-OR models.

In a yet further embodiment, the method further comprises: merging a node from the plurality of first nodes with its corresponding node in the plurality of second nodes so as to simplify the twin model.

In a yet further embodiment, the method further comprises: merging a node from the plurality of first nodes with its corresponding node in the plurality of second nodes so as to simplify the twin model.

In a yet further embodiment, after setting the intervention node of the plurality of second nodes in the twin model to a value, the method further comprises: when a node from the plurality of second nodes has identical latent variables and identical parent nodes as its corresponding node in the plurality of first nodes, merging the node with its corresponding node so as to simplify the twin model.

FIG. 1 is a schematic of a diagnostic system. In one embodiment, a user 1 communicates with the system via a mobile phone 3. However, any device could be used, which is capable of communicating information over a computer network, for example, a laptop, tablet computer, information point, fixed computer etc.

The mobile phone 3 will communicate with interface 5. Interface 5 has 2 primary functions, the first function 7 is to take the words uttered by the user and turn them into a form that can be understood by the inference engine 11. The second function 9 is to take the output of the inference engine 11 and to send this back to the user's mobile phone 3.

In some embodiments, Natural Language Processing (NLP) is used in the interface 5. NLP helps computers interpret, understand, and then use every day human language and language patterns. It breaks both speech and text down into shorter components and interprets these more manageable blocks to understand what each individual component means and how it contributes to the overall meaning, linking the occurrence of medical terms to the Knowledge Graph. Through NLP it is possible to transcribe consultations, summarise clinical records and chat with users in a more natural, human way.

However, simply understanding how users express their symptoms and risk factors is not enough to identify and provide reasons about the underlying set of diseases. For this, the inference engine 11 is used. The inference engine is a powerful set of machine learning systems, capable of reasoning on a space of more than hundreds of billions of combinations of symptoms, diseases and risk factors, per second, to suggest possible underlying conditions. The inference engine can provide reasoning efficiently, at scale, to bring healthcare to millions.

In an embodiment, the Knowledge Graph 13 is a large structured medical knowledge base. It captures human knowledge on modern medicine encoded for machines. This is used to allow the above components to speak to each other. The Knowledge Graph keeps track of the meaning behind medical terminology across different medical systems and different languages.

In an embodiment, the patient data is stored using a so-called user graph 15.

Clinical diagnostic models (CDMs) can be probabilistic graphical models (PGMs) that model hundreds of diseases, risk factors (the causes of diseases), and symptoms, as binary nodes.

Figure 2:
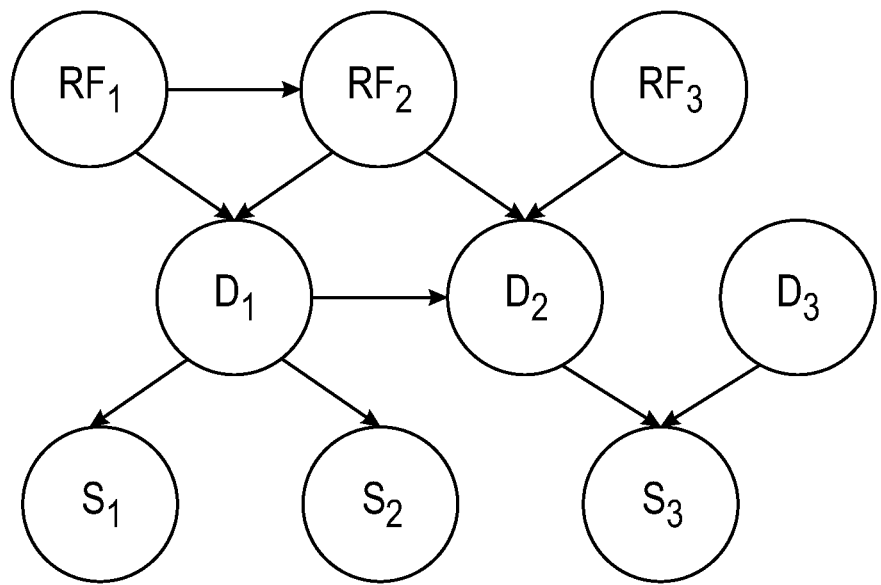
FIG. 2 is a diagram of a probabilistic graphical model of the type that can be used with the system of FIG. 1.

FIG. 2 is a depiction of a graphical model of the type used in the system of FIG. 1.

The graphical model provides a natural framework for expressing probabilistic relationships between random variables, to facilitate causal modelling and decision-making. In the model of FIG. 2, when applied to diagnosis, D stands for diagnosis, S for symptom and RF for Risk Factor. Three layers: risk factors, diseases and symptoms. Risk factor causes (with some probability) influence other risk factors and diseases, diseases causes (again, with some probability) other diseases and symptoms. There are prior probabilities and conditional marginals that describe the "strength" (probability) of connections. In embodiments, Noisy-OR and Noisy-MAX modelling assumptions are used.

Most widely used is the Noisy-OR assumption, as it closely fits the belief about how diseases develop, and allows large PGMs to be efficiently learned and stored. For a variable Y with parents $X_1, \ldots, X_N$, Noisy-OR assumes that Y=1 if any of its parents activate it. A parent $X_i$ activates its child if i) the parent is 'on', $X_i=1$, and ii) the activation succeeds, with an independent probability of failure $\lambda_{X_i, Y}$. Further details of the Noisy-OR model are provided below.

In this simplified specific example, the model is used in the field of diagnosis. In the first layer, there are three nodes $S_1$, $S_2$ and $S_3$, in the second layer there are three nodes $D_1$, $D_2$ and $D_3$ and in the third layer, there are three nodes $RF_1$, $RF_2$ and $RF_3$.

In the graphical model of FIG. 2, each arrow indicates a dependency. For example, $D_1$ depends on $RF_1$ and $RF_2$. $D_2$ depends on $RF_2$, $RF_3$ and $D_1$. Further relationships are possible. In the graphical model shown, each node is only dependent on a node or nodes from a different layer. However, nodes may be dependent on other nodes within the same layer.

In an embodiment, the graphical model of FIG. 2 is a Bayesian Network or probabilistic graphical model "PGM". In this Bayesian Network (or PGM), the network represents a set of random variables and their conditional dependencies via a directed acyclic graph. Thus, in the network of FIG. 2, given full (or partial) evidence over symptoms $S_1$, $S_2$ and $S_3$ and risk factors $RF_1$, $RF_2$ and $RF_3$ the network can be used to represent the probabilities of various diseases $D_1$, $D_2$, and $D_3$.

Causal knowledge is crucial for effective reasoning in many areas of science and medicine. This is due to the fact that causal relations, unlike correlations, allow one to analyse the consequences of interventions and treatments. When performing a primary diagnosis, a clinician aims to explain a patients presented symptoms by determining the most likely underlying diseases causing them. Despite this, all previous approaches to Machine Learning assisted diagnosis, including both model-based Bayesian and Deep Learning approaches, fail to incorporate causal knowledge in the diagnosis procedure. The embodiments described herein detail a new diagnostic method based on counterfactual inference, which captures the causal aspect of diagnosis overlooked by previous approaches. Whilst previous approaches fail to match human doctors, the counterfactual method achieves expert clinical accuracy.

The embodiments described herein are largely concerned with the PGM. Specifically, methods are presented which instead of using posterior ranking, a counterfactual measure is instead used and inference is performed on this.

Structural causal models (SCMs) can represent variables as functions of their direct causes, along with an unobserved 'noise' variable that is responsible for their randomness.

To understand the differences, a background on PGMs will be given:

Definition 1. A structural causal model (SCM) specifies:

1) a set of independent latent variables $U=\{u_1; \ldots; u_n\}$ distributed according to $$P(U) = \prod_i p(u_i),$$

2) a set of observed variables $V=\{v_1; \ldots; v_n\}$;

3) a directed acyclic graph G, called the causal structure of the model, whose nodes are the variables $U \cup V$; and 4) a collection of functions $F=\{f_1; \ldots; f_n\}$ such that every observed variable is a function of its parents together with a latent 'noise' term;

$$v_i = f_i(Pa(v_i); u_i);$$

where $Pa_i$ denotes the parent nodes of the $i^{th}$ observed variable from G.

The latent noise term appearing in each $f_i$ can be suppressed into $Pa(v_i)$ by enforcing the convention that every observed node has an independent latent variable as a parent in G without loss of generality. This convention is adopted throughout the following.

As every observed variable has an independent latent variable as a parent, the distribution over latents induces a distribution over observed variables through the functions F.

That is $$p(v_i) = \sum_{u|v_i=f_i(u)} P(u).$$

As P(U) factorises over each element of U, the joint distribution over every node in G factors into conditional distributions for each variable given its parents $$P(v_1, \ldots, v_n, u_1, \ldots, u_m) = \prod_i p(v_i \mid Pa_i) \prod_k p(u_k).$$

Hence, once all exogenous latent variables are marginalized over, an SCM describes a Bayesian network. Any Bayesian network can be constructed in this manner from some underlying SCM. Conversely, SCMs can be viewed as a refinement of Bayesian networks to include the details of the underlying generative functions—a redundant feature in Bayesian networks when calculating observational probabilities but vital for calculating counterfactuals.

In order to formally define a counterfactual query, a "do-operator," an interventional primitive is first defined.

Consider a SCM with functions F. The effect of intervention do(X=x) in this model corresponds to creating a new SCM with functions $F_{X=x}$, formed by deleting from F all functions $f_i$ corresponding to members of the set X and replacing them with the set of constant functions X=x. That is, the do-operator forces variables to take certain values, regardless of the original causal mechanism. Probabilities involving the do-operator, such as P(Y=y|do(X=x)) corresponds to evaluating ordinary probabilities in the SCM with functions $F_X$, in this case P (Y=y).

Counterfactual queries tell us the probability that certain outcomes would have occurred had some precondition been different. Given some observations $\mathcal{E}$ =e, the likelihood is calculated that a different outcome $\mathcal{E}$ =e' (counter to the facts of $\mathcal{E}$ =e) would have been observed given that some hypothetical intervention do(T=t) had taken place. Here do(T=t) is used to denote the intervention to fix variable T=t as defined by Pearl's calculus of interventions [27]. This counterfactual is summarised by the probability $$P(\varepsilon = e' | \varepsilon = e, do(T = t))$$

Counterfactuals allow the quantification of the causal affect of hypothetical interventions on latent variables. For example, it could be asked what is the likelihood that a symptom would not be present, given that the symptom is observed and a disease D, in some unknown state, was treated. This is determined by the counterfactual probability P(S=F|S=T, do(D=F)). If D=T is likely to be causing S=T, i.e. the disease is a good causal explanation of the symptom, then this probability will be high. On the other hand, disease hypotheses that are likely given the symptoms but a poor causal explanation will result in low probabilities.

Definition 2 (Counterfactual). Let X and Y be two subsets of variables in V. The counterfactual sentence "Y would be y (in situation U), had X been x," is the solution Y=y of the set of equations $F_x$, succinctly denoted $Y_x$ (U)=y.

As with observed variables in Definition 1, the latent distribution P(U) allows one to define the probabilities of counterfactual statements.

$$P(Y_x = y) = \sum_{u|Y_x(u)=y} P(u). \quad (1)$$

It is possible to implement an algorithmic procedure for computing arbitrary counterfactual queries. First, the distribution over latents is updated to account for the observed evidence. Second, the do-operator is applied. Third, the new causal model created by the application of the do-operator in the previous step is combined with the updated latent distribution to compute the counterfactual query.

The above steps can be summarised as follows (where $\mathscr{E}$ denotes the set of real evidence):

(1) (abduction) The distribution of the exogenous latent variables P(u) is updated to obtain $P(u|\mathscr{E})$.

(2) (action) Apply the do-operation to the variables in set X, replacing the equations $X_i = f_i(Pa(x_i), u_i)$ with $X_i = x_i \forall X_i \in X$.

(3) (prediction). Use the modified model to compute the probability of Y=y.

The first step, updating the distribution over latents and storing the resulting probabilities, requires a large amount of computational resources and memory—especially as conditioning on evidence induces correlations between initially uncorrelated latents. Moreover, as this step has to be repeated for every new counterfactual query, such computational resources are continually required. Therefore, the first step, in updating the exogenous latents, is intractable for large models with significant tree-width such as diagnostic networks.

In an embodiment, it is possible to avoid this computationally expensive step by reducing the computing of counterfactual statements to performing Bayesian inference on an associated causal model, known as a twin network.

The twin network method employs two interlinked networks, one representing the real world and the other the counterfactual world being queried. These two networks are identical in structure and share the same latent variables—as the latents are not modified by interventions on the observed variables. The observable variables from the original model are duplicated and labeled distinctly, as they may obtain different values in the real and counterfactual models. After the counterfactual world undergoes the desired intervention, computing a counterfactual statement in the original model is reduced to performing Bayesian inference in the twin network, as the variables in the real and counterfactual worlds can be explicitly compared. The construction of twin networks is discussed further below.

In Pearl, J. 2018. Theoretical impediments to machine learning with seven sparks from the causal revolution. arXiv preprint arXiv:1801.04016), Pearl refers to a "hierarchy" of queries that can be asked about probabilistic models: associative/observational, causal, and counterfactual.

Associative queries lie at the first level of the hierarchy, allowing us only to ask purely observational or "what happened" questions.

This is the domain of Bayesian networks and statistics. Causal queries lie at the second level and concern asking interventional, or "what if", questions, formalised using the do-operator. At the top of the hierarchy are counterfactual, or "why", questions. These allow us to ask causal questions about hypothetical interventions, whilst taking into account real evidence—often in apparent contradiction to our desired interventions.

Consider the question "I have not taken an Asprin, A=false. If I had, would my headache H have gone away?".

This query can be written as $p(H_{A=true}=false|A=false)$ where $H_{A=a}$ is 'the value of H if A had taken value a'.

Note that the evidence state, A=true, differs from the hypothetical intervention state Â=false—a feature that cannot be represented by any purely causal or observational question. Although we posit a different hypothetical state Â=true to the evidence state A=false, the evidence state is still relevant as it provides information about other variables in our model, such as confounding influences between A and H. It is this feature that separates counterfactual queries from causal queries Diagnosis—Posterior Ranking Diagnosis can be performed using a CDM by posterior ranking. Given a patients observed risk-factors R and symptoms S, the posteriors of all model diseases are computed, p(Di=T|R,S), and the most likely diseases returned as a differential. Other factors may be used as well as the posterior likelihood in constructing the final differential, such as disease cruelty, but the posteriors are the key ingredient supplied by the CDM.

Bayesian networks represent arguably the best method for performing algorithmic diagnosis—as they are interpretable and can model a very large number of diseases simultaneously.

The next section will explain how they are used to perform diagnosis via the ranking of disease posteriors given evidence, and give examples of where this approach fails to capture the true diagnostic procedure.

Figure 3:
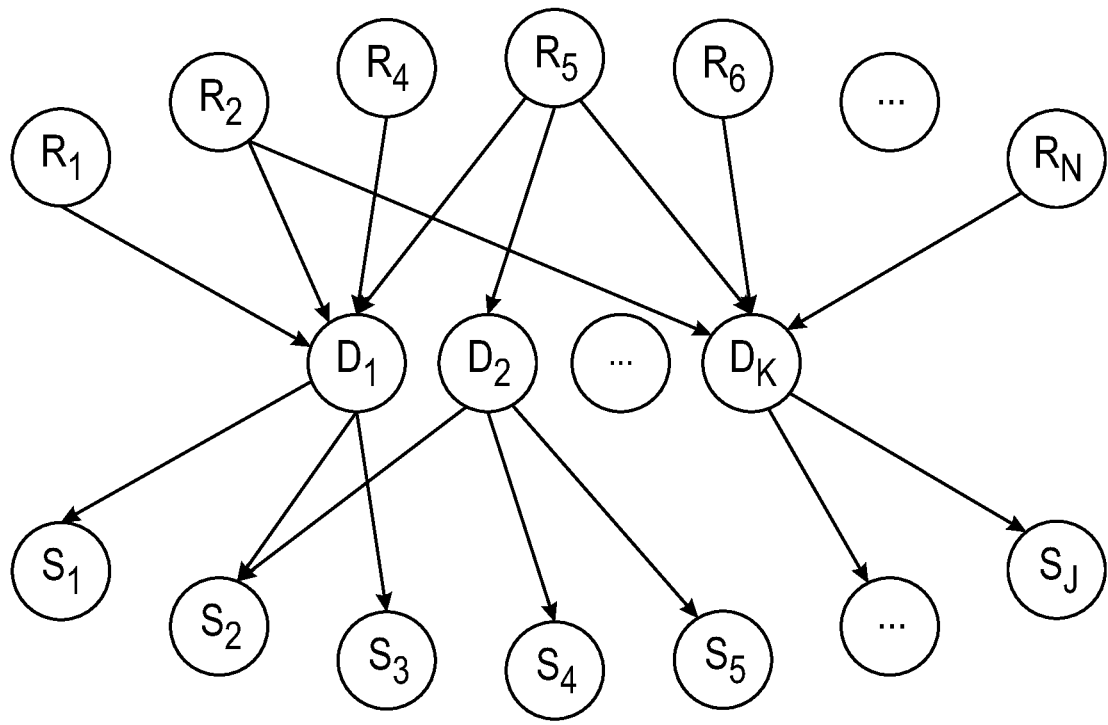
FIG. 3 is a diagram of a PGM for explaining the counterfactual diagnosis method in accordance with an embodiment.

FIG. 3 depicts a typical three-layer Bayesian network used for diagnosis. The top layer is populated by risk factor nodes, such as smoking or a family history of heart disease, representing variables that have a direct causal influence on the diseases. The diseases are found in the middle layer with the bottom layer corresponding to symptoms. For each disease, its children are the symptoms caused by that disease.

The top layer nodes are risk factors, which represent population variables, such as smoking and fitness, that have causal influences on diseases—which constitute the middle layer of nodes. The bottom layer correspond to symptoms, which are caused by underlying diseases. Thick wires highlight back-door paths between diseases $D_1$, $D_2$ and $D_K$.

FIG. 3 is just an example of one network. Simpler diagnostic networks can been employed, such as Bayesian networks which have no risk factor layer and stipulate no correlations between diseases. Networks with greater topological complexity can also be considered, such as those exhibiting disease-disease connections—allowing for inter-disease causal effects.

For the Diagnosis that is performed on three-layer networks as follows.

A patient supplies evidence which may include known risk factors, symptoms and possibly some known diseases.

These evidence states are denoted as $D_{obs}$; $R_{obs}$; $S_{obs}$. These observations are then applied to the network, and candidate (latent) diseases are ranked by their posteriors. That is, candidate diseases are ranked $\mathcal{D} = \{D_1, D_2; \ldots ; D_N\}$, such that:

$$P(D_i|D_{obs}, R_{obs}, S_{obs}) \geq P(D_{i+1}|D_{obs}, R_{obs}, S_{obs}), \forall i$$

This ranked list of diseases is then used to construct a diagnosis differential, a ranked list of diseases that should be tested for. This can be done in many ways, such as simply choosing the top N most likely diseases, or grading diseases in terms of cruelty to the patient and returning the top N for each cruelty grading. Regardless of how these diseases are ranked, the posterior ranking is the primitive ingredient of such differentials.

This approach correctly identifies the most likely diseases given the evidence. However, this is not necessarily what a doctor does when diagnosing a patient. A doctor seeks to diagnose the disease which they believe to be the underlying cause of the presented evidence. In certain cases, the most likely disease given the evidence does not correspond to the underlying cause of the evidence. If the task of diagnosis is to determine the disease which should be treated in order to reduce or remove the presented symptoms, then outputting the most likely disease will in some cases systematically return the wrong ordering of candidate diseases to treat.

The three-layer CDMs as shown in FIG. 3 have a richer probabilistic structure than the two layer BN2O networks, which model only diseases and symptoms, and make unphysical assumptions such as disease priors being independent. Whilst this additional structure makes these newer models far more accurate than their predecessors, unobserved risk factors result in confounding between diseases, leading to spurious conclusions being drawn if one relies solely on observational statistics (see below).

Confounding: Latent risk factors allow for back-door paths between diseases (e.g. the thick edges in FIG. 3.). This can lead to diseases that have little or nothing to do with the presented symptoms being ranked highly in the differential due to their large posterior correlation with the symptoms through backdoor paths.

In the example DAG depicted in FIG. 3, consider the case where $s_2$; $s_4$; $s_5$=true and all other symptoms are un-evidenced, that is=false. Disease $D_2$ is a parent of all of the evidenced symptoms and could constitute the most likely cause of the underlying symptoms (depending on the details of the model). Disease $D_1$ is a parent of $S_2$ only—it cannot constitute a causal explanation for symptoms $S_4$ and $S_5$, whereas disease $D_K$ is a parent of none of the evidenced symptoms. $D_K$ may be disregarded as it may not be a cause of the symptoms. However its posterior can be very high due to the back-door paths that it shares with $D_1$ and $D_2$.

Furthermore, if diseases like $D_1$ and $D_2$ are rare diseases such as cancer, with small priors and relatively small posteriors, $D_K$ can have a large enough posterior (or even prior) to make it impossible to discern rare but relevant diseases like $D_1$; $D_2$ from common, irrelevant diseases like $D_K$. Likewise the posterior weight of $D_1$ derives from a mixture of causative correlations with $S_2$ and backdoor correlations from sharing multiple risk-factor parents with $D_2$. Typically, it would be unlikely that $D_1$ is a good candidate disease for diagnosis, but it is simple to construct scenarios whereby $p(D_1|\varepsilon) \geq p(D_2|\varepsilon)$.

Counterfactual Ranking

In an embodiment, the counterfactual measure proposed—will be termed expected disablement—and is designed to rank diseases based on how well they explain the symptoms presented. As there are often multiple underlying diseases, it is too stringent to ask that all reported positive symptoms would disappear if it were not for a single disease (for example, if this disease is not a parent of one of these symptoms, the probability of disablement evaluates to 0). On the other hand, disease explanations that can explain as many symptoms as possible are favoured. To accommodate these two characteristics, the proposed measure takes the form of an expectation value.

Definition 3 (Expected disablement). The expected disablement of a disease $D_k$ with respect to evidence E is the number of "on" symptoms would be expected to be switched off if there was an intervention to 'cure' $D_k$, given $\varepsilon$ $$\mathbb{E}_D(D_k, \varepsilon) = \sum_{S \subseteq S_+} |S_+ - S| p(S^*_{D_k=0} = 0 \mid \varepsilon)$$

Where $S_+ = \{s \in S_{obs} \text{ s.t. } s=1\}$, $S_- = \{s \in s_{obs} \text{ s.t. } s=0\}$ and $\varepsilon = \{S_{obs}, D_{obs}, R_{obs}\}$. Here for notational connivance a superscript * is added to denote the counterfactual variable.

The expected disablement has three incredibly desirable properties that, mark it out as an important diagnostic measure.

Theorem 1 (Expected disablement decomposition). The expected disablement $\mathbb{E}_D(D_k; \varepsilon)$ can be written as:

$$\sum_{S \subseteq S_+} |S_+ - S| p(S^*_{D_k=0} = 0 \mid D_k = 1, \varepsilon) p(D_k = 1 \mid \varepsilon)$$

By Theorem 1, the expected disablement is an expectation value over the set of positively evidenced symptoms that are children of a given node, weighted by the 'causal effect' of $D_k$ on its children, and posterior of the disease given the evidence. It thus has the following three desirable properties.

1. Diseases with low posteriors are ranked low $$\lim_{p(D_k=1|\varepsilon) \to 0} \mathbb{E}_D(D_k, \varepsilon) = 0$$

2. Diseases that explain many symptoms are ranked higher than diseases that explain fewer symptoms:

$$\lim_{S_+ \cap Ch(D_k) \to \phi} \mathbb{E}_D(D_k, \varepsilon) = 0 \text{ and}$$

$$\mathbb{E}_D(D_k, \varepsilon) \leq S_+ \cap Ch(D_k)$$

3. Diseases with low 'causal effect' on the symptoms are ranked low:

$$P(S^*_{D_k=0} = 0 \mid \varepsilon, D_k = 1, \varepsilon) = 0 \Rightarrow \mathbb{E}_D(D_k, \varepsilon) = 0$$

where $S = \{\in S_+ \text{ s.t. } s \in Ch(D_k)\} S = fs$
The Causal approx of expected disablement:

$$\sum_{d_k} p(d_k \mid \varepsilon) |S - S_+| p(S \mid do(D_k = d_k))$$

this can be calculated without needing to know the functions

Next Noisy-OR models, a specific class of SCMs for Bernoulli variables that are widely employed as clinical diagnostic models, are defined. The Noisy-OR assumption states that a variable Y is the Boolean OR of its parents $X_1$, $X_2, \ldots, X_n$, where the inclusion or exclusion of each causal parent in the OR function is decided by an independent probability or 'noise' term. The standard approach to defining Noisy-OR is to present the conditional independence constraints generated by the Noisy-OR assumption.

$$p(Y = 0 \mid X_1, \ldots, X_n) = \prod_{i=1}^{n} p(Y = 0 \mid only(X_i = 1))$$

where $p(Y=0|only(X_i=1))$ is the probability that $Y=0$ conditioned on all of its (endogenous) parents being 'off' ($X_j=0$) except for $X_i$ alone. We denote $p(Y=0|only(X_i=1))=\lambda_{X_i,Y}$ by convention.

The utility of this assumption is that it reduces the number of parameters needed to specify a Noisy-OR network to $O(N)$ where N is the number of directed edges in the network. All that is needed to specify a Noisy-OR network are the single variable marginals $p(X_i=1)$ and, for each directed edge $X_i \to Y_j$, a single $\lambda_{X_i,Y_j}$. For this reason, Noisy-OR has been a standard assumption in Bayesian diagnostic networks, which are typically large and densely connected and so could not be efficiently learned and stored without additional assumptions on the conditional probabilities. The Noisy-OR assumption for SCMs is now defined.

Definition 4 (Noisy-OR SCM). A Noisy-OR network is an SCM of Bernoulli variables, where for any variable Y with parents $Pa(Y)=\{_1;:::;X_N\}$ the following conditions hold.

1. Y is the logical OR of its parents, where for each parent $X_i$ there is a Bernoulli variable $U_i$ whose state determines whether the parent is included in the OR function, or if it is ignored $$y = \bigvee_{i=1}^{N} (x_i \wedge \bar{u}_i)$$

i.e. $Y=1$ if any parent is on, $x_i=1$, and is not ignored, $u_i=0$ ($\bar{u}_i=1$ where 'bar' denotes the negation of $u_i$).

2. The probability of ignoring the state of a given parent variable is independent of whether any of the other parents have been ignored $$P(u_1, u_2, \ldots, u_N) = \prod_{i=1}^{N} P(u_i)$$

3. For every node Y their is a parent 'leak node' $L_Y$ that is singly connected to Y and is always 'on', with a probability of ignoring given by $\lambda_{L_Y}$ The inclusion of assumption 3 is a convention (a leak node is just a parent L for which $p(L=1)=1$). The leak node represents the probability that $Y=1$, even if $X_i=0 \forall X_i \in Pa(Y)$. For example, the leak nodes allow the situation that a disease spontaneously occurs to be modelled, even if all risk factors that are modelled are absent, or that a symptom occurs but none of the diseases that are modelled have caused it. Let us briefly consider the physical justification for the Noisy-OR assumption in modelling disease/symptom relationships, given Definition 4.

First, consider the assumption (1), that the generative function is a Boolean OR. This is equivalent to assuming that diseases or risk-factors never 'destructively interfere'. If $D_1$ is activating symptom S, and so is $D_2$, then this joint activation never cancels out to yield S=F. If two diseases are both activating a symptom, then the symptom is activated. Assumption 2 is also well justified in the clinical context. It states that a given disease (if present) has a fixed likelihood of activating a symptom, independent of the presence or absence of any other disease.

The above Noisy-OR assumptions allow great simplification of the model complexity, but also are fairly representative of how diseases/symptoms are expected to respond to their parent risk factors/diseases. For example, a symptom will be present if one parent disease, or another parent disease, is present. Furthermore, it is reasonable to expect that the probability that a symptom does not manifest, even if a parent disease is present, is (typically) independent of whether or not another disease is present.

Noisy-OR models are simple to learn from observational statistics. The latent priors, along with the single-variable priors, constitute all of the parameters needed to specify a Noisy-OR model. The following standard notation is used for the latent variable probabilities.

$$p(u_{X_i,Y_j}=0)=\lambda_{X_i,Y_j} \quad (4)$$

Given the conditional probability distributions for single parent-child pairs, determining these latent priors (and hence fitting a Noisy-OR model) is a computationally simple task.

Theorem 2 (Learning Noisy-OR models). Lambdas can be calculated from pairwise conditional probability tables as $$\lambda_{X_i,Y_j} = \frac{p(Y_j = 0 \mid X_i = 1)}{p(Y_j = 0 \mid X_i = 0)} \quad (5)$$

As Noisy-OR models can be learned from single and two-variable statistics alone, they are particularly appealing for learning diagnostic models from epidemiological data, which usually comes in the form of double-blind studies involving small sets of variables.

As Noisy-OR models are typically presented as Bayesian networks, the above definition of Noisy-OR is non-standard. Below it is shown that the SCM definition yields the Bayesian network definition, (3).

Theorem 3 (Noisy-OR CPT). The conditional probability distribution of a child Y given its parents $\{X_1, \ldots, X_n\}$ and obeying Definition 14 is given by $$p(Y = 0 \mid X_1 = x_1, \ldots, X_n = x_n) = \prod_{i=1}^{n} \lambda_{X_i,Y}^{x_i}$$

Proof. For $Y=0$, the negation of y, denoted $\bar{y}$, is given by $$\bar{y} = \neg \left( \bigvee_{i=1}^{N} (x_i \wedge \bar{u}_i) \right) = \bigwedge_{i=1}^{N} (\bar{x}_i \vee u_i)$$

The CPT is calculated from the structural equations by marginalizing over the latents, i.e. all latent states that yield $Y=0$ are summed over. Equivalently, it is possible to marginalize over all exogenous latent states multiplied by the above Boolean function, which is 1 if the condition $Y=0$ is met, and 0 otherwise.

$$p(Y = 0 \mid X_1 = x_1, \ldots, X_n = x_n) = \sum_{u_Y} \bigwedge_{i=1}^{N} (\bar{x}_i \vee u_i) p(u_Y)$$

$$= \sum_{u_{X_i,Y}} \prod_{X_i} (\bar{x}_i \vee u_i)$$

$$\prod_{U_{X_i,Y}} p(u_{X_i,Y})$$

$$= \prod_{X_i} \sum_{u_{X_i,Y}} p(u_{X_i,Y})(\bar{x}_i \vee u_i)$$

-continued $$= \prod_{X_i} [p(u_{X_i,Y} = 1) + p(u_{X_i,Y} = 0)\tilde{x}_i]$$

$$= \prod_{X_i} [\lambda_{X_i,Y} + (1 - \lambda_{X_i,Y})\tilde{x}_i]$$

$$= \prod_{X_i} \lambda_{X_i,Y}^{x_i}$$

This is identical to the Noisy-OR cpt (3).

Next, the expected disablement for Noisy-OR models will be derived. Above, there is a discussion of Pearl's algorithmic procedure for computing the probability of arbitrary counterfactuals.

The first step of this procedure, updating the distribution over latents and storing the resulting probabilities, requires a large amount of computational resources and memory. As this step has to be repeated for every new counterfactual query, the computational overheads can be quite costly. To overcome this, a twin network can be used.

Twin Networks: Twin networks are constructed by taking two copies of the original PGM (e.g. SCM), one to represent real variables and another to represent their counterfactual states. The two copies are linked by sharing exogenous latent variables (in the case of Noisy-OR, these are the noise terms $u_i$) between corresponding nodes. The counterfactual is then computed by applying a do-operation on the counterfactual graph and using belief propagation on the resulting model.

Figure 4A:
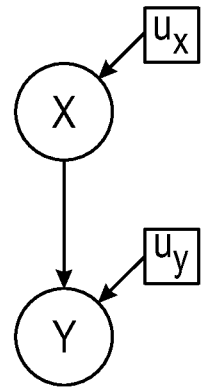
FIGS. 4($a$)-4($c$) are diagrams for explaining a twin network.
Figure 4B:
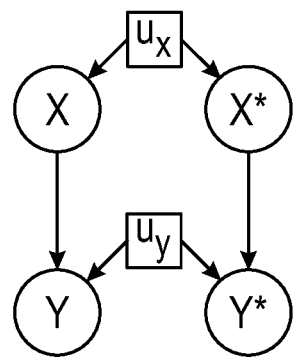

The construction of the twin network is illustrated in FIGS. 4 and 5.

Figure 4C:
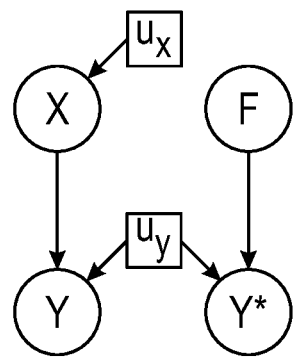

FIG. 4 shows a simple example. FIG. 4(a) shows a structural causal model for two observed variables X, Y and their exogenous latents $u_X$, $u_Y$. FIG. 4 (b) illustrates the construction of the twin network, with X*, Y* representing the counterfactual states of X, Y. FIG. 4(c) shows the twin network under a hypothetical intervention setting do(X*=F). The counterfactual P(Y*|Y,do(X*=F)) is calculated from (c) using standard belief propagation.

FIG. 5 shows another example of how a twin network is formed. FIG. 5 (a) shows the original PGM/SCM. In this example, the PGM has a directed acyclic graph structure, and comprises a feed-forward, three layer network. The top layer nodes represent risk factors $R_1 \ldots R_N$. The second layer nodes represent diseases $D_1 \ldots D_M$. The third layer nodes represent symptoms $S_1 \ldots S_L$. This model assumes no directed edges between nodes belonging to the same layer.

Figure 5A:
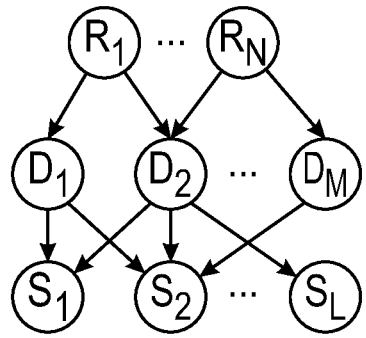
FIGS. 5($a$)-5($e$) are diagrams for explaining a twin network.
Figure 5B:
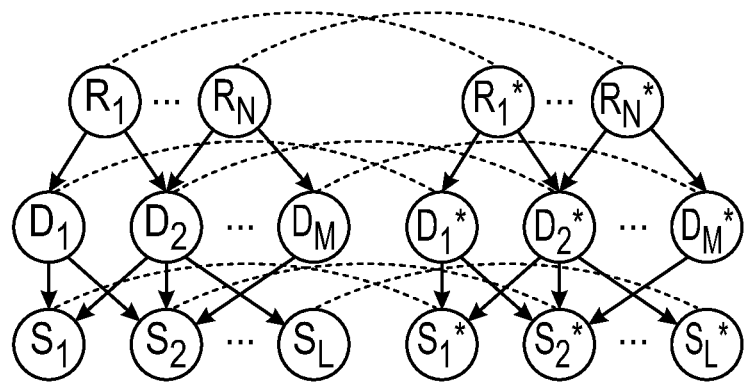
Figure 5C:
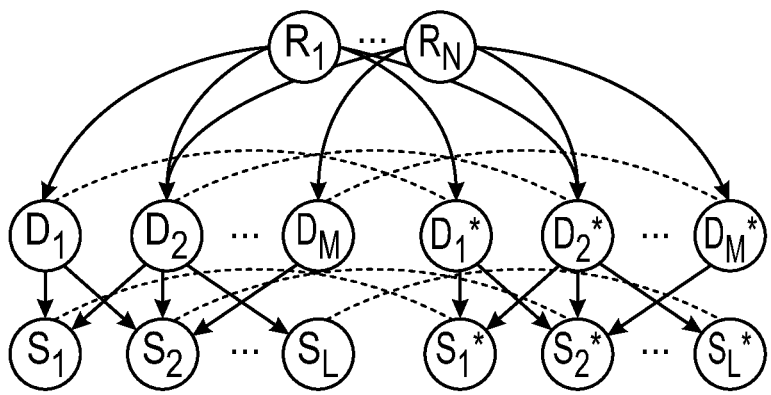

To construct the twin network, first the SCM as shown in FIG. 5(a) is copied so that there are two networks as shown in FIG. 5(b). In FIG. 5(b) the network on the left will encode the real evidence in a counterfactual query. This network is referred to as the 'real' graph.

The network on the right in FIG. 5(b) will take the hypothetical interventions and will yield the hypothetical observations. This network is referred to as the 'hypothetical' graph.

Pairs of copied variables are referred to as dual nodes. The nodes on the hypothetical graph denoted X* where X is the corresponding 'dual' node on the real graph. For example, in FIG. 5(b) $R_1$ and $R^*_1$ are dual nodes. Also, $D_1$ and $D^*_1$ are dual nodes.

The twin network of FIG. 5 (b) is constructed such that each node on the real graph shares its exogenous latent with its dual node, so $u^*_{Xi} = u_{Xi}$. These shared exogenous latents are depicted as dashed lines in FIG. 5 (b) to (e).

A disease node is selected in the hypothetical graph to perform the intervention on. In the example shown in FIG. 5 (b), the disease node $D^*_2$ is selected in the hypothetical graph to perform the intervention on.

Blue circles indicate observations, whereas red circles indicate interventions.

Applying the do-operation do(D*=0) to the hypothetical disease node D* cuts any directed edges going into D* and fixes D*=0, as shown in FIG. 5 (d) below.

Once the hypothetical intervention has been applied, it is possible to greatly simplify the twin network graph structure via node merging. In SCM's a node is fully determined given an instantation of all of its parents and its exogenous latent. Hence, if two nodes have identical exogenous latents and parents, they are copies of each other and can be merged into a single node.

By convention, when dual nodes are merged there is a mapping X*→X (dropping the asterisk). Dual nodes which share no ancestors that have been intervened upon can therefore be merged.

Figure 5D:
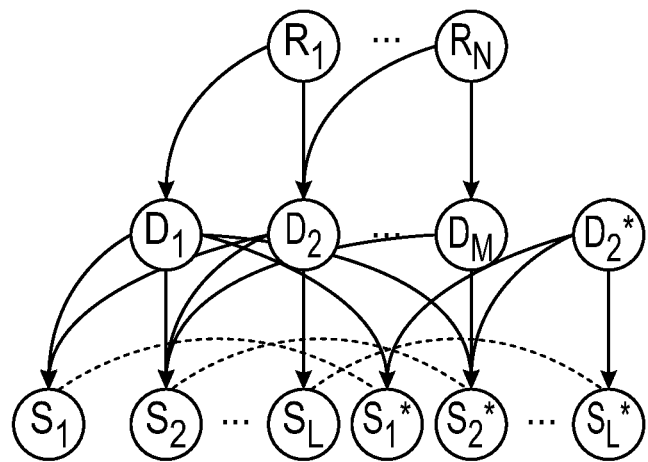
Figure 5E:
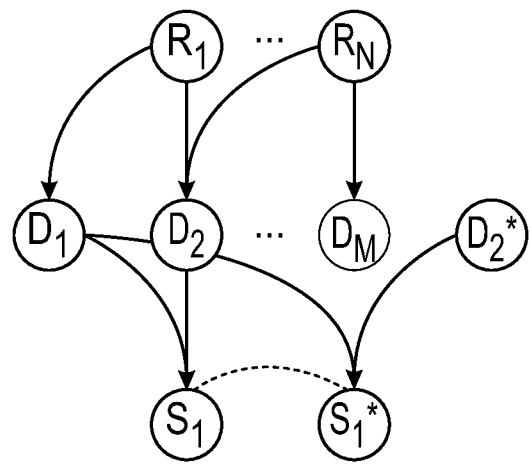

As interventions are not performed on the risk factor nodes, all ($R_i$, $R^*_i$) are merged (as shown in FIG. 5(d). Note that for the sake of clarity the exogenous latents for risk factors are not depicted in FIG. 5 (c)-(d).

Alternatively, because the risk factor nodes ($R_i$, $R^*_i$) are not children of the intervention node ($D^*_2$ which is a disease node), the risk factor nodes ($R_i$, $R^*_i$) can be merged before applying the intervention, as shown in FIG. 5 (c).

Following this, all corresponding real/hypothetical disease nodes that have no intervention ancestors can be merged, as their latents and parents are identical (shown in FIG. 5 (d)).

Finally, any symptoms that are not children of the disease that has been intervened upon can be merged, as again their latent and all of their parent variables are identical. In FIG. 5 (d), only $S_1$ has any evidence applied to it. As the symptoms are at the bottom of the graph, if they are un-evidenced they can be removed (this is true for all graphical models when doing inference). So only $S_1$ and its dual $S_1^*$ remain.

The resulting twin network is depicted in FIG. 5 (e). In FIG. 5(e), $D_M$ is shown as being greyed out. This is because it is not a parent of any of the symptoms. Thus, just like the symptoms that were removed as described above, it is at the bottom of the network and unevidenced. So it is superfluous to the task of inference and hence can be removed. This is the case for all nodes that are not parents of the symptoms.

Counterfactuals are then computed from the posteriors on this twin network. For example in FIG. 5(e), the counterfactual $p(S_{1D_1=0}=0|S_1=1)$ is given by $p(S_1^*=0|S_1=0, D_2^*=0)$.

This approach massively amortizes the standard inference cost of calculating counterfactuals by abduction, action and prediction, which would otherwise be intractable for large clinical diagnostic models (CDMs).

Noisy-OR Twin Networks

A Noisy-OR SCM (for example that is described above) can be used to derive the conditional probability tables (CPTs) on the twin network. The only CPTs that differ from the original Noisy-OR SCM are those for unmerged dual symptom nodes (i.e., children of the intervention node DK). In one embodiment, the diagnostic twin network is feed-forward and as such the disease layer forms a Markov blanket for the symptoms layer, d-separating dual symptom pairs from each other. As a result, the CPTs for dual symptoms and their parent diseases alone are derived.

Lemma 1: For a given symptom S and its hypothetical dual S*, with parent diseases D and under the hypothetical intervention do(D*k=0), the joint conditional distribution on the twin network is given by $$p(s, s^* \mid \mathcal{D}_{\setminus k}, D_k, do(D_k^* = 0)) = \begin{cases} p(s = 0 \mid \mathcal{D}) & \text{if } s = s^* = 0 \\ 0 & \text{if } s = 0, s^* = 1 \\ \left(\frac{1}{\lambda_{D_k,s}} - 1\right) p(s = 0 \mid \mathcal{D}_{\setminus k}, D_k = 1) \delta(d_k - 1) & \text{if } s = 1, s^* = 0 \\ p(s = 1 \mid \mathcal{D}_{\setminus k}, D_k = 1)/\lambda_{D_K,s} & \text{if } s = 1, s^* = 1 \end{cases}$$

where $\delta(d_k - 1) = 1$ if $D_k = 1$ else 0, and $D = \mathcal{D}_{\setminus k} \cup D_k$, i.e. $\mathcal{D}_{\setminus k}$ is the set of diseases that are not intervened on.

The proof for the above Lemma can be found in the Appendix.

When comparing counterfactual and posterior diagnosis, improved diagnostic accuracy should not come at the expense of greater computational cost. To overcome this issue, a closed form expression is now derived for the expected disablement in Noisy-OR diagnostic networks that only requires knowledge of the observational statistics, as is the case for posterior ranking.

Lemma 1 reduces the counterfactual query to an observational query on the original Noisy-OR network, with some simple adjustments to the conditional probabilities. We want to evaluate the expected disablement of the hypothetical intervention do(D*$_k$=0), which is defined as $$\mathbb{E}_{D_K, \varepsilon} := \sum_{S'} |S_+ - S'_+| p(S' \mid \varepsilon, do(D_k = 0))$$

where the sum enumerates over all possible S', the hypothetical symptom states that are consistent with the real evidence $\mathcal{E}$ and the intervention do(D$_k$=0). S$_\pm$ denote the positive/negative symptoms in the evidence set S. The intervention do(D$_k$=0) can never switch on symptoms, so one need only enumerate over hypothetical symptoms states where S'$_+ \subseteq$S$_+$ as these are the only counterfactual states with non-zero weight. From this it also follows that for all s∈S$_- \Rightarrow$ s*∈S'$_-$. Expressing the counterfactual (17) as a query on the twin network, the positive/negative symptoms on the hypothetical graph are denoted as S*$_\pm$. The counterfactual posterior in (17) is represented on the twin network as $$\rho(S_+^*, S_-^*, \mid E, do(D_k^* = 0)) = \rho(S_+^*, S_-^* \mid S_+, S_-, \mathcal{R}_{obs} = r, do(D_k^* = 0))$$

Theorem 4 (Noisy-OR expected disablement). The expected disablement of intervention $\hat{D}_k^* = 0$ can be written $$\mathbb{E}_{\hat{D}_k} = \frac{1}{p(S_+, S_-)} \sum_{X \in S_+} (-1)^{|S_+|-|X|} \Lambda_{X,k}$$

$$\sum_{s \in X} \frac{1 - \lambda_{sk}}{\lambda_{sk}} \times P(S_- = 0, X_{\hat{D}_k = 0} = 0, D_k = 1 \mid \mathcal{R}_{obs})$$

where $X_{\hat{D}_k = 0}$ means $s_{\hat{D}_k = 0} \forall s \in X$ and $\Lambda_{X,k} = \prod_{s \in X} \lambda_{k,s}$.

Alternatively, the theorem can be expressed as follows: For the Noisy-OR networks described above, the expected disablement of disease $D_k$ is given by $$E_{D_K, \varepsilon} = \frac{1}{p(S_+, S_- \mid \mathcal{R}_{obs} = r)} \sum_{C \subseteq S_+ \cap Ch(D_k)} |C| p(C = 0, S_\pm \setminus C \mid D_k = 1, \mathcal{R}_{obs} = r)$$

$$p(D_k = 1 \mid \mathcal{R}_{obs} = r) \frac{\prod_{S \in C}(\lambda_{D_k, S} - 1)}{\prod_{S \in S_+} \lambda_{D_k, S}}$$

where $S_\pm \setminus C$ denotes $S_- = 0, S_+ \setminus C = 1$.

The proof for the above equation can be found in the Appendix.

Note that as all common causes in the three-layer Noisy-OR diagnostic network are observed, the probability P(S$_-$=0, X$_{\hat{D}_k}$=0, D$_k$=1|R$_{obs}$) can be identified in terms of purely observational probabilities via the Backdoor criterion (Pearl, J. 2009. Causality (2nd edition). Cambridge University Press).

Experimentally Comparing Counterfactual and Posterior Diagnosis

Existing algorithms fail to incorporate causal knowledge in the diagnostic process. The counterfactual diagnosis measure captures this causal information.

To evaluate the effectiveness of our counterfactual diagnostic measure, a comparison of the diagnostic precision for the described CDM using posterior ranking and expected disablement ranking of diseases is performed.

The following definition of diagnosis is taken: the determination of the diseases that are most likely to be causing the observed symptoms. We devise a minimal criteria for desirable diagnostic measures to reflect this definition; i) M(Dk)→0 smoothly as P(Dk=T|E)→0 (consistency), ii) M(Dk)=0 for diseases that are not ancestors of any positive symptoms and therefore cannot constitute causal explanations for and observed symptoms (causality), and iii) diseases that explain a greater number of positive symptoms should be ranked highly (simplicity). From this criteria counterfactual diagnostic measure is selected as the expected disablement E(Dk), $$\mathbb{E}(D_K, \varepsilon) := \sum_{S'} |S_+ - S'_+| p(S' \mid \varepsilon, do(D_k = F))$$

Where E is the total evidence state, S+ denotes the set of positive symptom evidence, S' is a counterfactual symptom state with $S'+=\{S\in S'|S=T\}$. The expected disablement is the number of symptoms that one would expect to nullify, had one intervened to cure disease $D_k$.

The performance of the diagnostic measure are tested against a set of 600 clinical vignettes. These vignettes are produced by a panel of expert medical professionals, and contain a single ground-truth disease, a collection of symptoms and risk factors, and basic demographic information such as age and gender.

The symptom and risk factor evidence are selected by the expert panel to represent the evidence that could typically be presented to a doctor by a patient who has the vignette disease. Approximately half of the vignettes attempt to model rare diseases, whereas the other half model diseases of high incidence. The task of the diagnostic algorithm is to return a differential of N diseases ranked in terms of their likelihood given the evidence on each vignette. The same diagnostic model is used for evaluating each measure. This model is a Noisy-OR model containing 1300 nodes, constructed using expert knowledge and epidemiological data (Razzaki, S.; Baker, A.; Perov, Y.; Middleton, K.; Baxter, J.; Mullarkey, D.; Sangar, D.; Taliercio, M.; Butt, M.; Majeed, A.; et al. 2018. A comparative study of artificial intelligence and human doctors for the purpose of triage and diagnosis. arXiv preprint arXiv:1806.10698.).

As a simple test of diagnostic accuracy, the accuracy of the top-N differential for posterior and counterfactual ranking were compared, with respect to the ground truth disease. The accuracy is defined as the probability that the ground truth disease is within a differential of size N, for N=1; : : : ; 20.

Figures 6, 7:
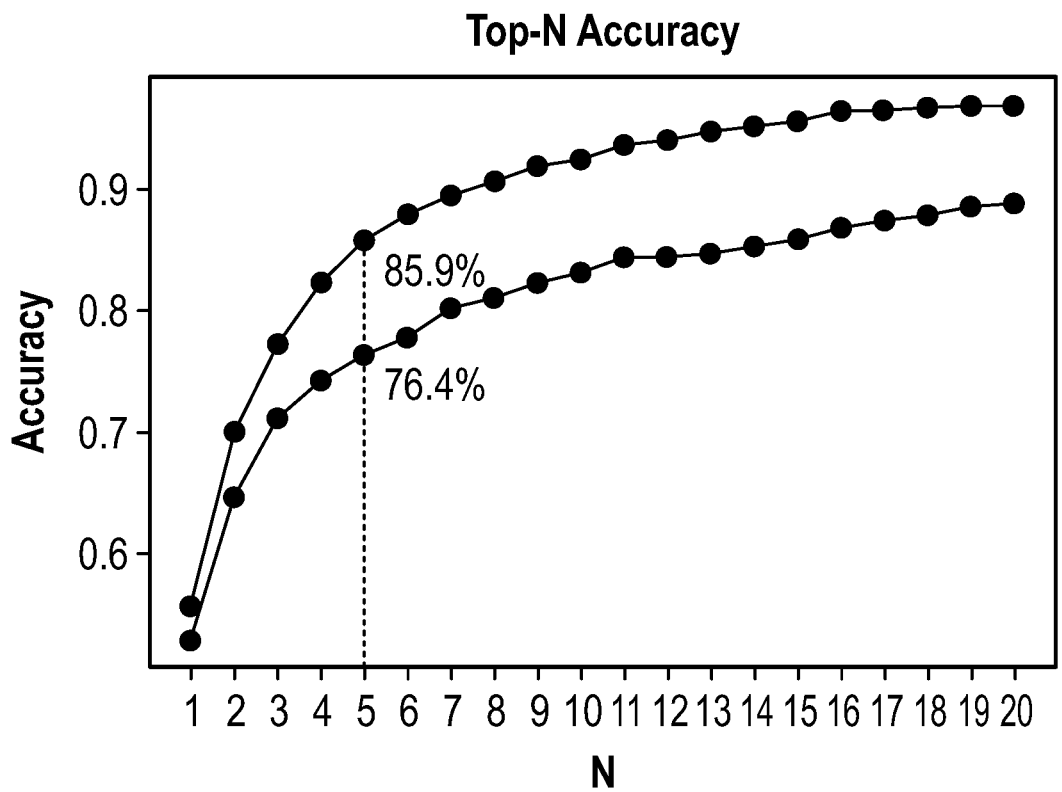
FIG. 6 is a plot showing a comparison of results for counterfactual ranking against posterior ranking.
FIG. 7 is a table showing a comparison of results for counterfactual ranking, posterior ranking and doctor ranking.

Given a differential $\mathcal{H}_M^{(N)} = \{D_1, D_2 \ldots D_N\}$ where $\mathcal{M}(D_i) \geq \mathcal{M}(D_{i+1})$ where $\mathcal{M}(.)$ is the chosen ranking measure, the accuracy of the ranking is simply calculated as the probability of the inclusion of the ground-truth disease $\mathcal{H}_M^{(N)}$ FIG. 6 shows the top-N accuracy of a Noisy-OR test model as calculated on 750 vignettes. As half of vignettes cover rare diseases, for which the ground truth disease should typically not be at the top of the ranking, rankings of N≥5 are focussed upon.

The top line represents the accuracy of differentials of size N for the counterfactual ranking, given by $\mathbb{E}_D(D; \varepsilon)$, and likewise for the lower line and posterior ranking $P(D; \varepsilon)$.

In this regime, using the counterfactual ranking approximately halves the error rate of the diagnosis compared to posterior ranking.

The two diagnostic measures are compared to the diagnoses of human doctors. For each case-card a diagnosis is gathered from four expert doctors, who are given each case card with the model disease masked and asked to provide a list of possible model diseases ranked from very likely to unlikely. All diseases that at least one doctor flagged as likely ($P(D=T|\mathcal{E} \geq 0.3$) are combined, and this is used as the 'ground truth' optimal diagnosis, as it represents the outcome of a 4th opinion expert consultation. For each doctor their precision is measured as the average fraction of the ground truth diseases for each case card that they predicted as likely, and likewise for the clinical diagnostic model (CDM) with $M(D_k, E) \geq 0.3$. Whilst this approach has an inherent bias towards doctors, as their assessment define the ground truth, it is necessary in order to model the inherent diagnostic uncertainty. Results are presented in the table of FIG. 7.

In general, the single limiting factor of counterfactual diagnosis is the requirement that the full structural causal model be known in order to compute the expected disablement. Indeed, in purely observational graphical diagnostic models, where the generative functions are unknown, the expected disablement may not be identifiable. However, there is a halfway house between posterior and full counterfactual diagnosis, given by interventional queries from the second level of the causal hierarchy. A simplified version of the quantity envisaged is as follows:

$$|P(S_{D=0}=0) - P(S=0)|P(D=1|S=1)$$

As all common causes in a three-layer Noisy-OR diagnostic network are observed, the above quantity can be identified in terms of purely observational probabilities via the Backdoor criterion, assuming the graphical structure of the network is known.

The above counterfactual diagnosis method can be used with any of the known approximate inference techniques, for example, Importance Sampling. The above inference technique can also be used with inference techniques described in Douglas et al "A Universal Marginalizer for Amortized Inference in Generative Models" arXiv: 1711.00695v1 [cs.LG] 2 Nov. 2017.

Figure 8:
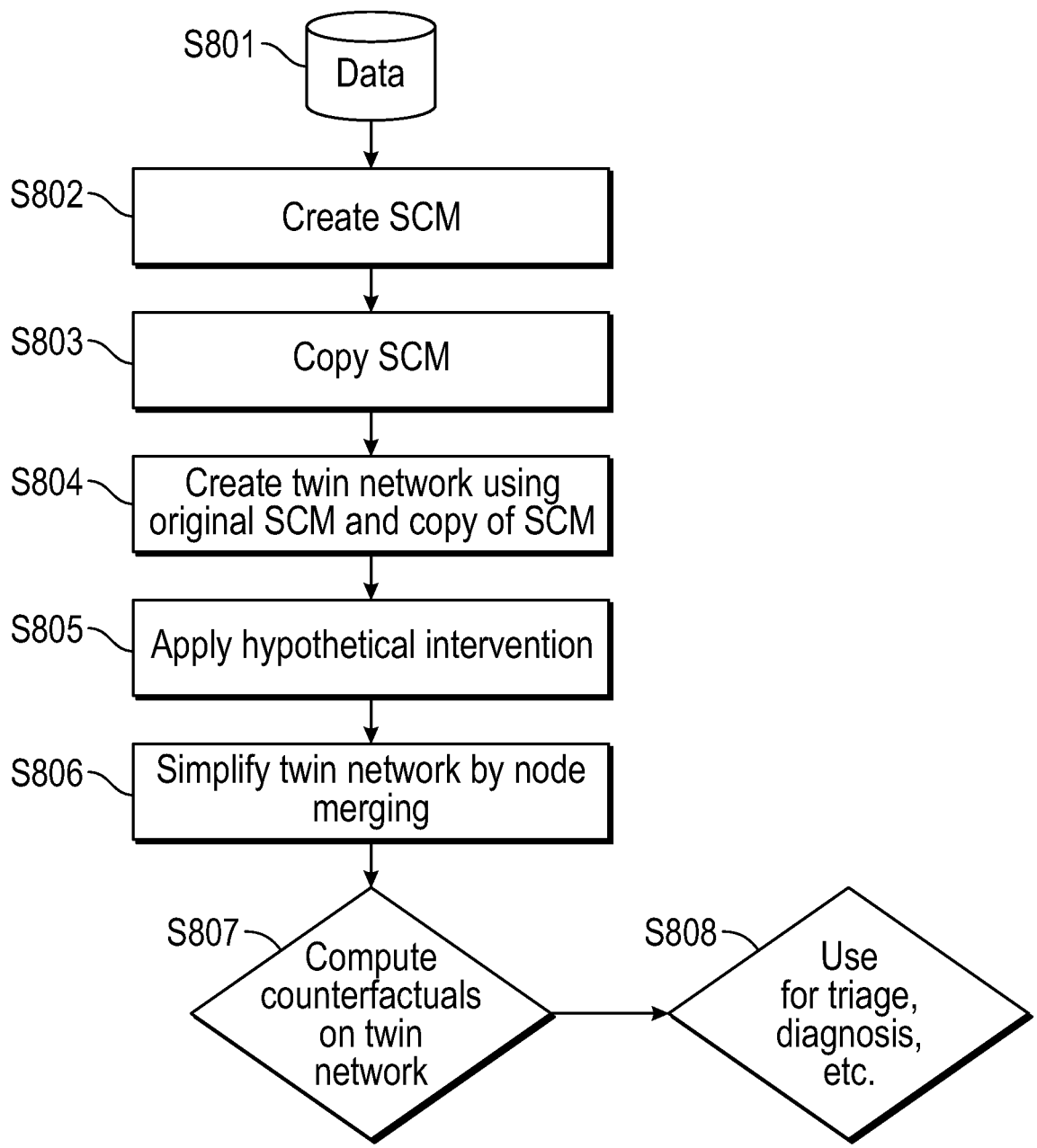
FIG. 8 is a flow chart depicting a method in accordance with an embodiment.

FIG. 8 is a flow chart depicting an embodiment of the counterfactual diagnosis method. In step S801, data is received. This data can be epidemiological data, expert knowledge, data from research studies or other data. A PGM, or SCM, is created (S802). The SCM may be a Noisy-OR SCM. A copy of the SCM is made in S803.

In step S804, the twin network is created using the original SCM from S802 and the copy from S803. Once the twin model is created, the hypothetical intervention can be applied (S805). Next, the twin network can be simplified through merging nodes (S806).

The twin network can then be used in the computation of counterfactuals (S807).

In step S808, the resultant PGM is then used for triage, diagnosis etc. For, example, this can be as described with reference to FIG. 9.

Figure 9:
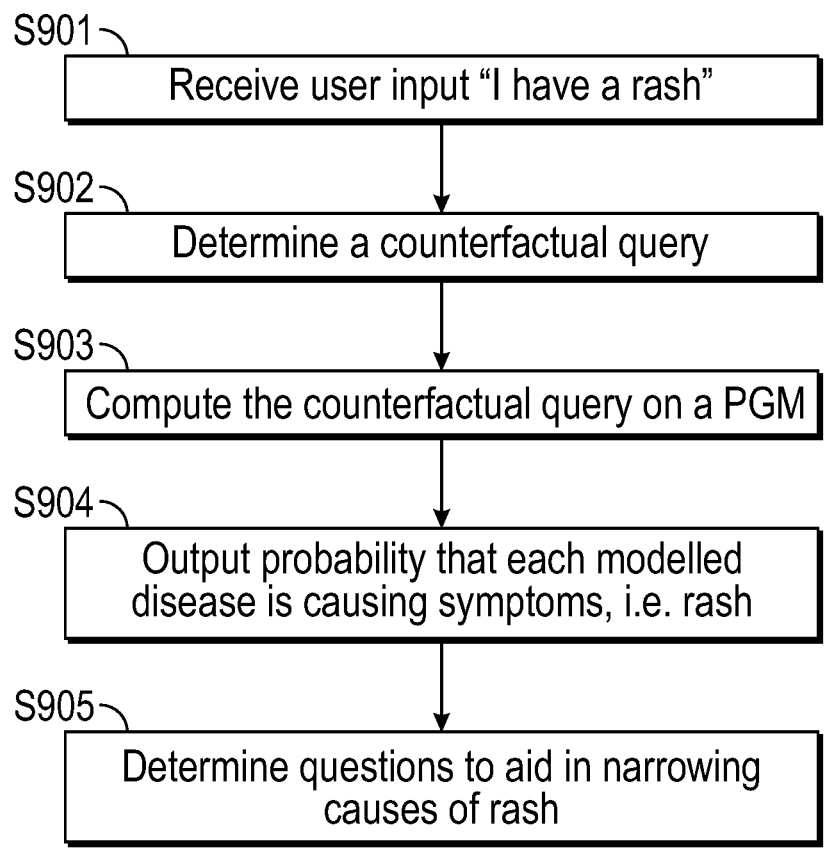
FIG. 9 is a flow chart showing a method in accordance with a further embodiment and FIG. 10 is a schematic of a system in accordance with an embodiment.

In step S901 of FIG. 9, the user inputs the phrase, for example, "I have a rash" into, for example, the mobile telephone of FIG. 1. This phrase is then passed to system and used to determine a counterfactual query (S902). The counterfactual query is then computed (S903) on the PGM through by identifying a node in the PGM that relates to the user's query. The PGM then outputs the probabilities that each modelled disease is causing the rash (S904).

The system may also determine further questions that will allow the possible causes for the user's symptoms to be narrowed (S905).

Figure 10:
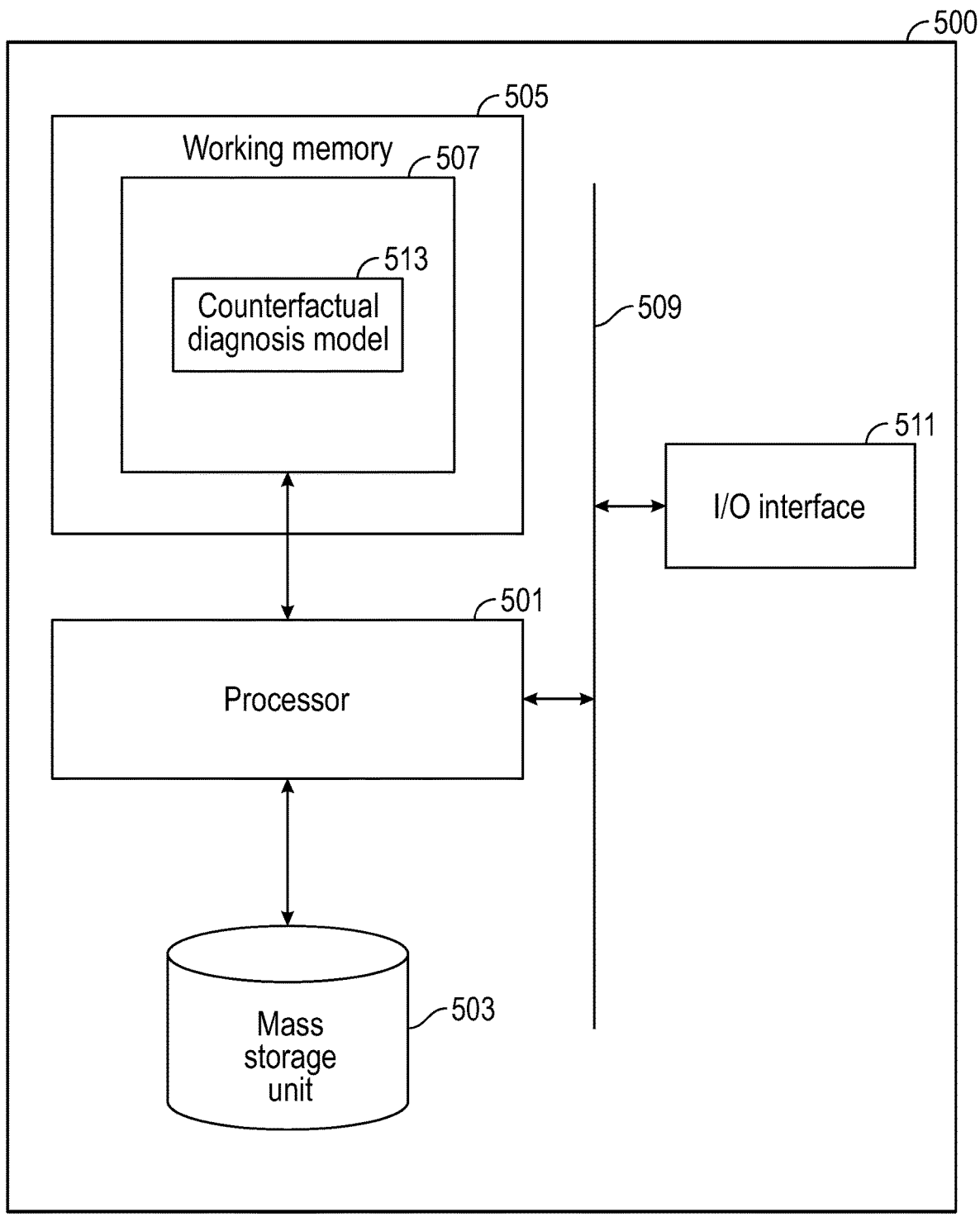

While it will be appreciated that the above embodiments are applicable to any computing system, an example computing system is illustrated in FIG. 10, which provides means capable of putting an embodiment, as described herein, into effect. As illustrated, the computing system 500 comprises a processor 501 coupled to a mass storage unit 503 and accessing a working memory 505. As illustrated, a counterfactual diagnosis model 513 is represented as software products stored in working memory 505. However, it will be appreciated that elements of the counterfactual diagnosis model 513, may, for convenience, be stored in the mass storage unit 503. Depending on the use, the counterfactual diagnosis model 513 may be used with a chatbot, to provide a response to a user question that requires the survival analysis model.

Usual procedures for the loading of software into memory and the storage of data in the mass storage unit 503 apply. The processor 501 also accesses, via bus 509, an input/output interface 511 that is configured to receive data from and output data to an external system (e.g. an external network or a user input or output device). The input/output interface 511 may be a single component or may be divided into a separate input interface and a separate output interface.

Thus, execution of the counterfactual diagnosis model 513 by the processor 501 will cause embodiments as described herein to be implemented.

The counterfactual diagnosis model 513 can be embedded in original equipment, or can be provided, as a whole or in part, after manufacture. For instance, the counterfactual diagnosis model 513 can be introduced, as a whole, as a computer program product, which may be in the form of a download, or to be introduced via a computer program storage medium, such as an optical disk. Alternatively, modifications to existing causal discovery model software can be made by an update, or plug-in, to provide features of the above described embodiment.

The computing system 500 may be an end-user system that receives inputs from a user (e.g. via a keyboard) and retrieves a response to a query using counterfactual diagnosis model 513 adapted to produce the user query in a suitable form. Alternatively, the system may be a server that receives input over a network and determines a response. Either way, the use of the counterfactual diagnosis model 513 may be used to determine appropriate responses to user queries, as discussed with regard to FIG. 1.

Implementations of the subject matter and the operations described in this specification can be realized in digital electronic circuitry, or in computer software, firmware, or hardware, including the structures disclosed in this specification and their structural equivalents, or in combinations of one or more of them. Implementations of the subject matter described in this specification can be realized using one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium (e.g., non-transitory carrier medium) can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

In the above embodiments, a purely directed causal discovery algorithm is converted into one that can also detect latent common causes. The modified algorithm is tested extensively on synthetic and real datasets. In the experiments explained above, the modified algorithm maintained the performance of the original algorithm on the directed datasets and allowed algorithms that originally could not detect latent causes to uncover them in both synthetic and real data.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of methods and systems described herein may be made without departing from the spirit of the inventions. The accompanying claims and their equivalents are intended to cover such forms of modifications as would fall within the scope and spirit of the inventions.

APPENDIX

Proof of Lemma 1

For a given symptom S and its hypothetical dual S*, with parent diseases $\mathcal{D}$ and under the hypothetical intervention $do(D_k^*=0)$, the joint conditional distribution on the twin network is given by $$p(s, s^* \mid \mathcal{D}_{\setminus k}, D_k, do(D_k^*=0)) =$$

$$\begin{cases} p(s=0 \mid \mathcal{D}) & \text{if } s = s^* = 0 \\ 0 & \text{if } s = 0, s^* = 1 \\ \left(\frac{1}{\lambda_{D_k,S}} - 1\right) p(s=0 \mid \mathcal{D}_{\setminus k}, D_k=1)\delta(d_k-1) & \text{if } s = 1, s^* = 0 \\ p(s=1 \mid \mathcal{D}_{\setminus k}, D_k=1)/\lambda_{D_k,S} & \text{if } s = 1, s^* = 1 \end{cases}$$

where $\delta(d_k-1)=1$ if $D_k=1$ else 0, and $\mathcal{D} = \mathcal{D}_{\setminus k} \cup D_k$, i.e. $\mathcal{D}_{\setminus k}$ the set of diseases that are not intervened on.

First, note that for this marginal distribution tin intervention $do(D_k^*=0)$ is equivalent to setting the evidence $D_k^*=0$ as we specify the full Markov blanket of $(s, s^*)$. Let us denote $\mathcal{D}_{\setminus k}$ as the set c parents of $(s, s^*)$ not inducting the intervention node $D_k^*$ or its dual $D_k$. We then need to compute the conditional probability $$p(s, s^* \mid \mathcal{D}_{\setminus k}, D_k^*=0, D_k) = \qquad (9)$$

$$\sum_{u_s} P(u_s) p(s \mid \mathcal{D}_{\setminus k}, D_k, u_s) p(s^* \mid \mathcal{D}_{\setminus k}, D_k^*=0, u_s)$$

The simplest way to calculate these conditional probabilities is by marginalization, i.e. we calculate $p(s=0, s^*=0 \mid \mathcal{D}, D_k^*=0, D_k)$, $p(s=0 \mid \mathcal{D}, D_k^*=0, D_k)$ and $p(s^*=0 \mid \mathcal{D}, D_k^*=0, D_k)$, and use these to construct all joint states. For $s_j=0$, the generative functions are given by $$p(s=0 \mid Pa(S), u_s) = u_L \wedge \bigvee_{x_i \in Pa(S)} (\bar{x}_i \vee u_{X_i,S}) \qquad (10)$$

First we compute the joint state.

$$p(s = 0 - D_k, D_k, u_s)p(s^* = 0 \mid D_k, D_k^*, u_s) = u_L \wedge$$

$$u_L \bigwedge_{D_k \in \mathcal{D}_{\setminus k}} (u_{D_k} S \vee \overline{d}_k) \bigwedge_{D_k \in \mathcal{D}_{\setminus k}} (u_{D_k} S \vee \overline{d}_j) \wedge [u_{D_k}, S \vee \overline{d}_k] \wedge [u_{D_k}, S \vee \overline{d}_k^*] =$$

$$u_L \bigwedge_{D_k \in \mathcal{D}_{\setminus k}} (u_{D_k}, S \vee \overline{d}_i)[u_{D_k}, S \vee (\overline{d}_k^* \wedge \overline{d}_k)]$$

Where we have used the Boolean identities $a \wedge a = a$ and $a \vee (b \wedge c) = (a \vee b) \wedge (a \vee c)$. Therefore $$p(s = 0, s^* \mid \mathcal{D}_{\setminus k}, D_k, D_k^*) =$$

$$\sum_{u_s} P(u_s)p(s = 0 \mid \mathcal{D}_{\setminus k}, D_k, u_s)p(s^* = 0 \mid \mathcal{D}_{\setminus k}, D_k^*, u_s) =$$

$$\lambda_{L_s}[\lambda_{D_k}, s(d_k \vee d_k^*) + \overline{d}_k \wedge \overline{d}_k^*] \prod_{D_i \in \mathcal{D}_{\setminus k}} [\lambda_{D_i}, sd_i + \overline{d}_i]$$

Next, we calculate the single-symptom conditionals $$p(s = 0 - \mathcal{D}_{\setminus k}, D_k) = \sum_{u_s} P(u_s)p(s = 0 \mid \mathcal{D}_{\setminus k}, D_k, u_s) =$$

$$\sum_{u_{L_s}} p(u_{L_s})u_{L_s} \prod_{D_i \in \mathcal{D}} \sum_{u_{D_k} S} p(u_{D_k} S)u_{D_k} S \bigvee \overline{d}_i =$$

$$p(u_{L_s} = 1) \prod_{D_i \in \mathcal{D}} \sum_{u_{D_k} S} [p(u_{D_i}, S = 1) + p(u_{D_i}, S = 0)\overline{d}_i] =$$

$$\lambda_{L_s} \prod_{D_i \in \mathcal{D}} [\lambda_{D_i}, sd_i + \overline{d}_i] \mathbb{1}$$

and similar for $p(s^* = 0 \mid \mathcal{D}_{\setminus k}, D_k^*)$. Note that $\lambda x + \overline{x} = \lambda^x$. We can now express the joint cpd over dual symptom pairs, using the identities $p(s=0, s^*=1|X) = p(s=0|X) \ldots p(s=0, s^*=0|X)$, $p(s=1, s^*=0|X) = p(s^*=0|X) \ldots p(s=0, s^*=0|X)$ and $p(s=1, s^*=1|X) = 1 - p(s=0|X) \ldots p(s^*=0|X) + p(s=0, s^*=0|X)$ for arbitrary X.

$$p(s, s^* \mid \mathcal{D}_{\setminus k}, D_k, D_k^*) =$$

$$\begin{cases} \lambda_{L_s} \lambda_{D_k, S}^{d_k \vee d_k^*} \prod_{D_i \in \mathcal{D}_{\setminus k}} \lambda_{D_i, S}^{d_i} & \text{if } s = s^* = 0 \\ \lambda_{L_s} \left[\lambda_{D_k, S}^{d_k} - \lambda_{D_k, S}^{d_k \vee d_k^*}\right] \prod_{D_i \in \mathcal{D}_{\setminus k}} \lambda_{D_i, S}^{d_i} & \text{if } s = 0, s^* = 1 \\ \lambda_{L_s} \left[\lambda_{D_k, S}^{d_k^*} - \lambda_{D_k, S}^{d_k \vee d_k^*}\right] \prod_{D_i \in \mathcal{D}_{\setminus k}} \lambda_{D_i, S}^{d_i} & \text{if } s = 1, s^* = 0 \\ 1 - \lambda_{L_s} \left[\lambda_{D_k, S}^{d_k} + \lambda_{D_k, S}^{d_k^*} - \lambda_{D_k, S}^{d_k \vee d_k^*}\right] \prod_{D_i \in \mathcal{D}_{\setminus k}} \lambda_{D_i, S}^{d_i} & \text{if } s = s^* = 1 \end{cases}$$

As we are always intervening to switch off diseases, $D_k^* = 0$, then $d_k \vee d_k^* = d_k$ and $$\lambda_{D_k, S}^{d_k} \ldots \lambda_{D_k, S}^{d_k \vee d_k^*} = 0 \quad (12)$$

and therefore $p(s=0, s^*=1 \mid \mathcal{D}_{\setminus k}, D_k, D_k^*=0) = 0$ as expected (switching off a disease will never switch on a symptom), This simplifies oar expression for the conditional distribution to $$p(s, s^* \mid \mathcal{D}_{\setminus k}, D_k, D_k^* = 0) = \begin{cases} \lambda_{L_s} \lambda_{D_k, S}^{d_k} \prod_{D_i \in \mathcal{D}_{\setminus k}} \lambda_{D_i, S}^{d_i} & \text{if } s = s^* = 0 \\ 0 & \text{if } s = 0, s^* = 1 \\ \lambda_{L_s} \left[1 - \lambda_{D_k, S}^{d_k}\right] \prod_{D_i \in \mathcal{D}_{\setminus k}} \lambda_{D_i, S}^{d_i} & \text{if } s = 1, s^* = 0 \\ 1 - \lambda_{L_s} \prod_{D_i \in \mathcal{D}_{\setminus k}} \lambda_{D_i, S}^{d_i} & \text{if } s = s^* = 1 \end{cases}$$

This then simplifies to $$p(s, s^* \mid \mathcal{D}_{\setminus k}, D_k, D_k^* = 0) =$$

$$\begin{cases} p(s = 0 \mid \mathcal{D}_{\setminus k}, D_k) & \text{if } s = s^* = 0 \\ 0 & \text{if } s = 0, s^* = 1 \\ p(s = 0 \mid \mathcal{D}_{\setminus k}, D_k = 0) - p(s = 0 \mid \mathcal{D}_{\setminus k}, D_k) & \text{if } s = 1, s^* = 0 \\ p(s = 1 \mid \mathcal{D}_{\setminus k}, D_k = 0) & \text{if } s = s^* = 1 \end{cases}$$

We have arrived at expressions for the cpt's over dual symptoms in terms of cpt's on the real graph, and hence our counterfactual query can be computed on the real graph alone. The third term in simplified conditionals, $p(s=0 \mid \mathcal{D}_{\setminus k}, D_k=0) - p(s=0 \mid \mathcal{D}_{\setminus k}, D_k)$, is identical to zero unless the free $D_K$ is in the stale $D_k=1$ in the real graph. Using definition of noisy-or def eq noisy or to give $$p(s = 0 \mid \mathcal{D}_{\setminus k}, D_k = 0) = \frac{1}{\lambda_{D_k, S}} p(s = 0 \mid \mathcal{D}_{\setminus k}, D_k = 1) \quad (15)$$

we recover $$p(s = 0 \mid \mathcal{D}_{\setminus k}, D_k = 0) - p(s = 0 \mid \mathcal{D}_{\setminus k}, D_k) = \quad (16)$$

$$\left(\frac{1}{\lambda_{D_k, S}} - 1\right) p(s = 0 \mid \mathcal{D}_{\setminus k}, D_k = 1)\delta(d_k - 1)$$

where $d_k$ the instantiation of $D_k$ on the real graph. The term $\delta(d_k \ldots 1)$ can be thought of as fixing the observation $D_k=1$ on the real graph. Finally, form the definition of the noisy-or cpt we have that $$p(s=1 \mid \mathcal{D}_{\setminus k}, D_k=0) = p(s=1 \mid \mathcal{D}_{\setminus k}, D_k=1)/\lambda_{D_K, S} \quad (17)$$

Proof of Theorem 4 (Noisy-OR Expected Disablement)

For the noisy-or networks described in Appendix A.1-A.4, the expected disablement of disease $D_k$ is given by $$E(D_K, \mathcal{E}) =$$

$$\frac{1}{p(S_+, S_- \mid \mathcal{R}_{obs} = r)} \sum_{C \subseteq S_+ \wedge CH_t(D_k)} |C| p(C = 0, S_\pm \setminus C \mid D_k = 1,$$

$$\mathcal{R}_{obs} = r)p(D_k = 1 \mid \mathcal{R}_{obs} = r) \frac{\prod_{S \in C}(\lambda_{D_k, S} - 1)}{\prod_{S \in S_+} \lambda_{D_s, S}}$$

where $S_\pm \setminus C$ denotes $S_- = 0$, $S_+ \setminus C = 1$.

From the above discussion, the non-zero contributions to expected disablement are $$E(D_K, \mathcal{E}) = \sum_{C \subseteq S_+} |C| p(S_-^\circ = 0, C^\circ = 0, S_+ \backslash C = 1 \mid S_+, S_-, \mathcal{R}_{obs} = r, \quad (21)$$

$$do(D_k^* = 0))$$

Applying Bayes rule, and noting the the real evidence states are not children of the intervention node $D_K^*$, gives $$E(D_K, \mathcal{E}) = \quad (22)$$

$$\frac{1}{p(S_+, S_- \mid R_{obs} = r)} \sum_{C \subseteq S_+} |C| p(S_-^* = 0, C^* = 0, S_+ \backslash C = 1,$$

$$S_+, S_- \mid \mathcal{R}_{obs} = r, do(D_k^* = 0))$$

Furthermore, by applying the inclusion-exclusion principle [58], we can expand this sum over the subsets $X \subseteq S_+ \backslash C$ give an expression tile right hand side of lil eq where all counterfactual variables are in the zero state $$E(D_K, \mathcal{E}) =$$

$$\frac{1}{p(S_+, S_- \mid R_{obs} = r)} \sum_{C \subseteq S_+} |C| \sum_{X \subseteq S_+ \backslash C} (-1)^{|S_+ \backslash C| - |X|} p(S_-^* = 0, C^* = 0,$$

$$X = 0, S_+, S_- \mid \mathcal{R}_{obs} = r, do(D_k^* = 0))$$

Let us now consider the probabilities $Q = p(S_-^* = 0, C^* = 0, S \backslash C^* = 1, S_+, S_- \mid \mathcal{R}_{obs} = r, do(D_k^* = 0))$. We can express these as marginalizations over the disease layer, which d-separate dual symptom pairs from each-other $$Q = \quad 24$$

$$\sum_{d, d_k} p(\mathcal{D}_{\backslash k} = d, D_k = d_k \mid R_{obs} = r) \prod_{S \in S_-} p(S^* = 0, S = 0 \mid \mathcal{D}_{\backslash k} = d,$$

$$D_k = d_k, D_k^* = 0) \times \prod_{S \in C} p(S^* = 0, S = 1 \mid \mathcal{D}_{\backslash k} = d,$$

$$D_k = d_k, D_k^* = 0) \prod_{S \in S_+ \backslash C} p(S^* = 1,$$

$$S = 1 \mid \mathcal{D}_{\backslash k} = d, D_k = d_k, D_k^* = 0)$$

Applying Lemma 1 simplifies this to $$Q = \sum_d p(\mathcal{D}_{\backslash k} = d, D_k = d_k \mid \mathcal{R}_{obs} = r) \prod_{S \in S_-} p(S = 0 \mid \mathcal{D}_{\backslash k} = d,$$

$$D_k = d_k) \prod_{S \in C} p(S = 0, \mid \mathcal{D}_{\backslash k} = d, D_k = 1) \delta(d_k - 1) \times$$

$$\prod_{S \in S_+ \backslash C} p(S = 1 \mid \mathcal{D}_{\backslash k} = d,$$

$$D_k = 1) \prod_{S \in C} \left( \frac{1}{\lambda_{D_k, S}} - 1 \right) \prod_{S \in S_+ \backslash C} \frac{1}{\lambda_{D_k, S}}$$

Note that the only Q in lil eq 2 that are not multiplied by a factor of zero have $C \neq \emptyset$, and so $\delta(d_k - 1)$ is always present. Marginalizing over $d_k$ and simplifying gives $$Q = p(S_- = 0, C = 0, S_+ \backslash C = 0, D_k = 1 \mid \mathcal{R}_{obs} = r) \frac{\prod_{S \in C} (\lambda_{D_k, S} - 1)}{\prod_{S \in C_+} \lambda_{D_k, S}} \quad (26)$$

Substituting this into lil eq 2 gives $$E(D_K, \mathcal{E}) = \frac{1}{p(S_+, S_- \mid R_{obs} = r)} \sum_{C \subseteq S_+} |C|(S_- = 0, \quad (27)$$

$$C = 0, S_+ \backslash C = 1, D_k = 1 \mid \mathcal{R}_{obs} = r) \frac{\prod_{S \in C} (\lambda_{D_k, S} - 1)}{\prod_{S \in S_+} \lambda_{D_k, S}}$$

Finally, noting that for any $S \in C$, $S \notin C$ $h(D_k)$, $\lambda_{D_k, S} - 1 = 0$, therefore the expectation can be reduced to one over all subsets of positively evidenced symptoms that are children of $D_k$. The final expression for the expected disablement is $$E(D_K, \mathcal{E}) = \frac{1}{p(S_+, S_- \mid R_{obs} = r)} \sum_{C \subseteq S_+ \cap Ch(D_k)} |C| p(C = 0,$$

$$S_\pm \backslash C \mid D_k = 1, R_{obs} r) p(D_k = 1 \mid \mathcal{R}_{obs} = r) \frac{\prod_{SC} (\lambda_{D_k, S} - 1)}{\prod_{S \in S_+} \lambda_{D_k, S}}$$

where $S_\pm \backslash C$ denotes $S_- = 0$, $S_+ \backslash C = 1$ and we have applied the chain rule to $D_k$.

Before proceeding, we can simplify exp dis significantly, $$E(D_K, \mathcal{E}) := \sum_{S'} |S_+ - S'_+| p(S' \mid \mathcal{E}, do(D_K = 0)) = \quad 29$$

$$\sum_{C \subseteq S_+} |C| p(S_- = 0, C = 0, S_+ \backslash C = 1 \mid \mathcal{E}, do(D_k = 0))$$

Next, we can expand the joint state using the inclusion\exclusion principle [58], expressing it as margianls over 0 states $$E(D_K, \mathcal{E}) := \sum_{C \subseteq S_+} |C| p(S_- =, 0, C = 0, S_+ \setminus C = 1 \mid \mathcal{E}, do(D_k = 0)) = \qquad (30)$$

$$\sum_{C \subseteq S_+} |C| \sum_{X \subseteq S_+ \setminus C} (-1)^{|S_+ \setminus C| - |X|} p(S_- = 0,$$

$$X = 0, C = 0 \mid \mathcal{E}, do(D_k = 0))$$

Next, denote $A := X \vee C$.

We with to count the number of occurrences of the marginal $p(S_-=0, \mathcal{A}=0|\varepsilon, do(D_k=0))$ in partial sum. Clearly, $\mathcal{A}$ varies over all subsets of $S_+$. For fixed $\mathcal{A}$, valid $\mathcal{C}$ that generate $\mathcal{A}$ varies over all subsets of $\mathcal{A}$, and for given $\mathcal{C}$, X is fixed to $X = \mathcal{A} \setminus \mathcal{C}$. Therefore, in partial sum, the coefficient of $p(S_-=0, \mathcal{A}=0|\varepsilon, do(D_k=0))$ is $\Sigma\,\mathcal{C} \subseteq \mathcal{A}\,|\mathcal{C}|(-1)^{|S_+\setminus C|-|\mathcal{A}\setminus\mathcal{C}|}$. As $\mathcal{C} \subseteq S_+$ and $X \subseteq \mathcal{A}$, then $|S_+\setminus \overline{\mathcal{C}}|-|\mathcal{A}\setminus\mathcal{C}|=|S_+|-|\mathcal{A}|$. Finally, using $$\sum_{k=0}^{N} k \binom{N}{k} = N 2^{N-1} \qquad (31)$$

we recover $$E(D_K, \mathcal{E}) = \sum_{A \subseteq S_+} (-1)^{|S_+|-|A|} |A| 2^{|A|-1} p(S_- = 0, \qquad (32)$$

$$A = 0 | \mathcal{E}, do(D_k = 0))$$

The invention claimed is:

1. A method for providing a computer implemented medical diagnosis, the method comprising:
   receiving an input from a user comprising at least one symptom of the user;
   providing the at least one symptom as an input to a medical model, the medical model being retrieved from memory, the medical model comprising: a probabilistic graphical model comprising probability distributions and causal relationships between symptoms and diseases;
   performing counterfactual inference on the probabilistic graphical model to obtain a prediction of the probability that the user has a disease; and
   outputting a counterfactual measure determined from the counterfactual inference,
   wherein the counterfactual measure is the expected number of symptoms that would not be present if a disease was treated,
   wherein the probabilistic graphical model is a twin network, the twin network formed by:
      creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;
      creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and
      combining the first graphical representation and the second graphical representation by the sharing of exogenous causes to create said twin network.

2. The method of claim 1, wherein a counterfactual measure is an expected disablement.

3. The method of claim 1, wherein the probabilistic graphical model is a Noisy-OR model.

4. The method of claim 1, wherein a counterfactual measure is an expected disablement and the probabilistic graphical model is a Noisy-OR model.

5. The method of claim 1, wherein performing counterfactual inference comprises using a discriminative model pre-trained to approximate the probabilistic graphical model, the discriminative model being trained using samples from said probabilistic graphical model;
   deriving estimates, from the discriminative model, that the user has a disease; and
   performing approximate inference on the probabilistic graphical model to obtain an indication that the user has that disease using the estimate from the discriminative model.

6. The method of claim 1, wherein the results of predictions of the diseases from the probabilistic graphical model are ranked using a counterfactual measure.

7. The method of claim 1, wherein the probabilistic graphical model is a twin network, a counterfactual measure is an expected disablement and the probabilistic graphical model is a Noisy-OR model.

8. A system for providing a computer implemented medical diagnosis, the system comprising a processor and a memory, the processor being adapted to:
   receive an input from a user comprising at least one symptom of the user;
   provide the at least one symptom as an input to a medical model, the medical model being retrieved from memory, the medical model comprising:
   a probabilistic graphical model being stored in memory comprising probability distributions and causal relationships between symptoms and diseases,
   perform counterfactual inference on the probabilistic graphical model to obtain a prediction of the probability that the user has a disease; and
   output a counterfactual measure determined from the counterfactual inference,
   wherein, the counterfactual measure is the expected number of symptoms that would not be present if a disease was treated,
   wherein the probabilistic graphical model is a twin network, the twin network formed by:
      creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;
      creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

9. A non-transitory carrier medium comprising computer-readable instructions being adapted to cause a computer to perform:

receiving an input from a user comprising at least one symptom of the user;

providing the at least one symptom as an input to a medical model, the medical model being retrieved from memory, the medical model comprising: a probabilistic graphical model comprising probability distributions and causal relationships between symptoms and diseases;

performing counterfactual inference on the probabilistic graphical model to obtain a prediction of the probability that the user has a disease; and outputting a counterfactual measure determined from the counterfactual inference, wherein, the counterfactual measure is the expected number of symptoms that would not be present if a disease was treated, wherein the probabilistic graphical model is a twin network, the twin network formed by:

creating a first graphical representation from a set of data, the first graphical representation comprising a plurality of first nodes indicating symptoms, risk factors and diseases, the first graphical representation indicating a relationship between the symptoms, the risk factors and the diseases, the first graphical representation indicating real variables;

creating a second graphical representation, wherein the second graphical representation is a copy of the first graphical representation, the second graphical representation comprising a plurality of second nodes indicating the symptoms, the risk factors and the diseases, the second graphical representation indicating counterfactual states of the real variables; and combining the first graphical representation and the second graphical representation by the sharing of exogenous causes to create said twin network.

10. The non-transitory carrier medium of claim 9, wherein a counterfactual measure is an expected disablement.

11. The non-transitory carrier medium of claim 9, wherein the probabilistic graphical model is a Noisy-OR model.

12. The method of claim 1, wherein the counterfactual inference further comprises:

updating a distribution of exogenous latent variables in the twin network based on the at least one symptom:

applying a do-operation to a node indicating the disease in the second graphical representation of the updated twin network; and computing a probability that the user would have the disease based on the updated twin network.

* * * * *